US009844419B2

(12) United States Patent
Andreiko

(10) Patent No.: US 9,844,419 B2
(45) Date of Patent: Dec. 19, 2017

(54) CUSTOM ORTHODONTIC APPLIANCE SYSTEM AND METHOD

(71) Applicants: Ormco Corporation, Orange, CA (US); Jean Andreiko

(72) Inventor: Craig A. Andreiko, late of Alta Loma, CA (US)

(73) Assignee: Ormco Corporation, Orange, CA (US)

( * ) Notice: Subject to any disclaimer, the term of this patent is extended or adjusted under 35 U.S.C. 154(b) by 893 days.

(21) Appl. No.: 13/972,880

(22) Filed: Aug. 21, 2013

(65) Prior Publication Data

US 2014/0067335 A1    Mar. 6, 2014

Related U.S. Application Data

(60) Division of application No. 13/282,130, filed on Oct. 26, 2011, which is a division of application No. 12/114,968, filed on May 5, 2008, now abandoned, which is a continuation of application No. 10/528,036, filed as application No. PCT/US03/30917 on Sep. 26, 2003, now Pat. No. 8,512,037.

(60) Provisional application No. 60/916,189, filed on May 4, 2007, provisional application No. 60/413,712, filed on Sep. 26, 2002.

(51) Int. Cl.
*A61C 7/00* (2006.01)
*A61C 7/12* (2006.01)
*A61C 7/14* (2006.01)

(52) U.S. Cl.
CPC .............. *A61C 7/002* (2013.01); *A61C 7/12* (2013.01); *A61C 7/146* (2013.01); *Y10T 29/49568* (2015.01)

(58) Field of Classification Search
CPC ..... A61C 7/00; A61C 7/002; A61C 2007/004; G05B 2219/2652; G05B 2219/45167
USPC ......................................................... 433/24
See application file for complete search history.

(56) References Cited

U.S. PATENT DOCUMENTS

| | | | |
|---|---|---|---|
| 4,249,897 A | 2/1981 | Anderson | |
| 4,531,911 A | 7/1985 | Creekmore | |
| 4,975,052 A | 12/1990 | Spencer et al. | |
| 5,131,843 A | 7/1992 | Hilgers et al. | |
| 5,322,435 A | 6/1994 | Pletcher | |

(Continued)

FOREIGN PATENT DOCUMENTS

| | | | |
|---|---|---|---|
| EP | 0502227 A1 | 9/1992 | |
| EP | 0696444 A2 | 2/1996 | |

(Continued)

OTHER PUBLICATIONS

European Patent Office, Supplementary Search Report in EP Application No. EP03798798, dated Feb. 6, 2008.

(Continued)

*Primary Examiner* — Yogesh Patel
(74) *Attorney, Agent, or Firm* — Wood Herron & Evans LLP

(57) ABSTRACT

Various features are provided for a custom orthodontic appliance manufacturing or designing system. These include features for inputting of data of patient anatomy and practitioner decisions, features for interactively or automatically manipulating data to arrive at applicant characteristics, and features for affecting design or manufacture of the appliance.

18 Claims, 44 Drawing Sheets

(56) References Cited

U.S. PATENT DOCUMENTS

| | | | |
|---|---|---|---|
| 5,368,478 A * | 11/1994 | Andreiko | A61C 7/00 433/24 |
| 5,431,562 A | 7/1995 | Andreiko et al. | |
| 5,447,432 A | 9/1995 | Andreiko et al. | |
| 5,464,347 A | 11/1995 | Allesee | |
| 5,464,349 A * | 11/1995 | Andreiko | A61C 7/282 433/17 |
| 5,533,895 A | 7/1996 | Andreiko et al. | |
| 5,820,370 A | 10/1998 | Allesee et al. | |
| 5,882,192 A | 3/1999 | Bergersen | |
| 5,991,728 A | 11/1999 | DeBusk et al. | |
| 6,227,850 B1 | 5/2001 | Chishti et al. | |
| 6,244,861 B1 * | 6/2001 | Andreiko | A61C 7/00 433/3 |
| 6,315,553 B1 | 11/2001 | Sachdeva et al. | |
| 6,463,344 B1 | 10/2002 | Pavloskaia et al. | |
| 6,733,289 B2 | 5/2004 | Manemann et al. | |
| 6,783,360 B2 | 8/2004 | Chishti | |
| 6,988,889 B2 | 1/2006 | Abels et al. | |
| 7,155,373 B2 | 12/2006 | Jordan et al. | |
| 7,264,468 B1 | 9/2007 | Kesling et al. | |
| 7,927,360 B2 | 4/2011 | Pond, Jr. et al. | |
| 8,512,037 B2 | 8/2013 | Andreiko | |
| 2002/0025503 A1 * | 2/2002 | Chapoulaud | A61C 7/00 433/24 |
| 2005/0003321 A1 | 1/2005 | Wiechmann et al. | |
| 2005/0175955 A1 | 8/2005 | Niederwanger et al. | |
| 2006/0057533 A1 | 3/2006 | McGann | |
| 2006/0105286 A1 | 5/2006 | Raby et al. | |
| 2006/0147871 A1 | 7/2006 | Brosius | |
| 2006/0147872 A1 | 7/2006 | Andreiko | |
| 2008/0038683 A1 | 2/2008 | Von Mandach | |

FOREIGN PATENT DOCUMENTS

| | | |
|---|---|---|
| WO | 9410935 A1 | 5/1994 |
| WO | 00/19935 A1 | 4/2000 |
| WO | 0069357 A1 | 11/2000 |
| WO | 03/073382 A1 | 9/2003 |
| WO | 2006/073699 A2 | 7/2006 |
| WO | 01/47405 A2 | 7/2011 |

OTHER PUBLICATIONS

Japanese Patent Office, English Translation of Office Action, from corresponding Japanese Application No. 2004-540292, dated Dec. 16, 2008.

Japanese Search Report, Japanese Application No. 2009-145868 filed Sep. 26, 2003, dated Aug. 2, 2011, with translation of points.

* cited by examiner

Root Angle Data

Root Angle Data

½ treated as maxillary extraction ⟷ ½ treated as no extraction

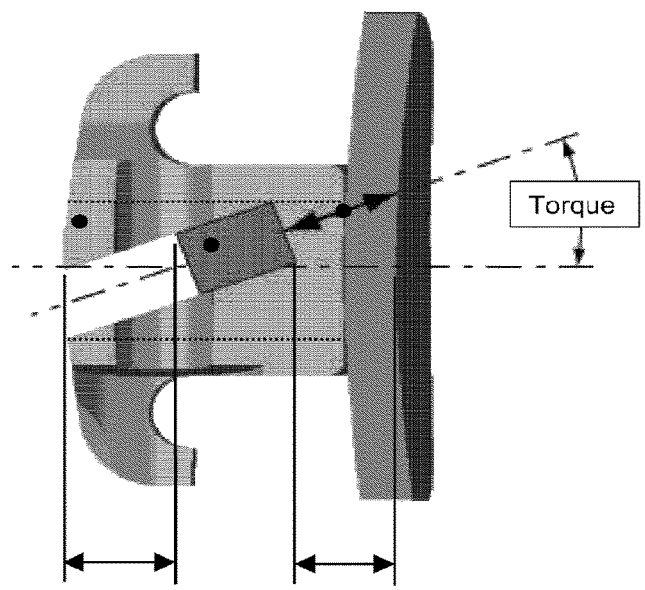
FIG. 41
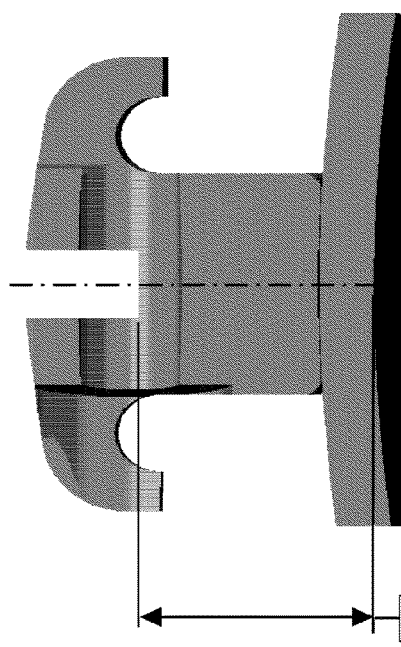 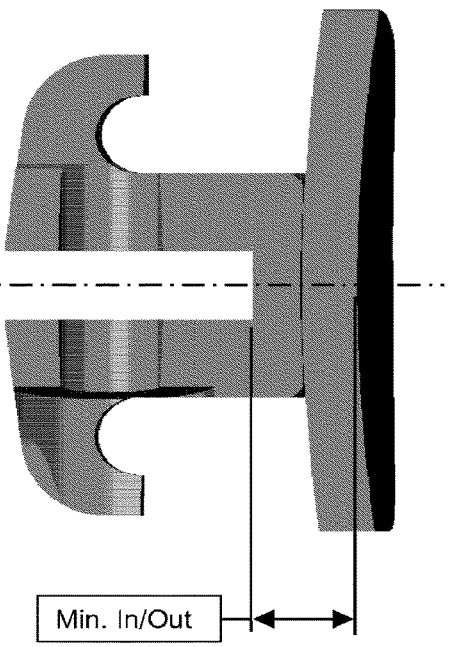
FIG. 42A        FIG. 42B

CUSTOM ORTHODONTIC APPLIANCE SYSTEM AND METHOD

RELATED APPLICATIONS

This application claims priority to U.S. application Ser. No. 13/282,130 filed Oct. 26, 2011, U.S. application Ser. No. 12/114,968 filed May 5, 2008, U.S. application Ser. No. 10/528,036 filed Dec. 2, 2005, now U.S. Pat. No. 8,512,037, issued Aug. 20, 2013, which application claims priority to U.S. Provisional Patent Application Ser. No. 60/413,712, filed Sep. 26, 2002, which is incorporated herein in its entirety.

FIELD OF THE INVENTION

This invention relates to orthodontic appliances for straightening the teeth of patients and more particularly to the use of computerized systems for determining the ideal orthodontic treatment of a patient's teeth to providing optimum orthodontic appliances for such treatment.

BACKGROUND OF THE INVENTION

Systems and methods for providing custom orthodontic appliances are described, for example, in U.S. Pat. No. 5,431,562 and in Published International patent application No. PCT/US00/35558. The practical implementation of such systems and methods benefits from improvements in software and computer interfaces, from accommodation of the priorities and preferences of orthodontic practitioners and from extended adaptation to the anatomy of the patient, both the individual anatomy and generic anatomical features.

There is a need for practical and economical improvements in the delivery of custom orthodontic appliances.

SUMMARY OF THE INVENTION

A number of features for providing orthodontic appliances are set forth herein to solve problems set forth above and otherwise. According to principles of the present invention, features of a custom orthodontic appliance method and system are presented for this and continuing or divisional applications. These features are set forth in this summary and also below in the detailed description and in the drawings.

The invention includes a method of representing a three dimensional tooth object for use in determine an orthodontic setup of the teeth. The method takes into account, groove and cusp points of lower molars to define line segments for orienting-these teeth, including calculating an arrangement using the stolar line.

A method of forming a digital image of a tooth is provided by scanning the tooth or a model thereof and adding tooth root data to the tooth object three dimensional data of one or more individual tooth roots. Such data may be of the individual patient's tooth root shapes or from library files. The information is joined with crown scan data, which may be collected separate from the root data. A scaled down image of the root may be expanded and modified to fit to the tooth crown and form a single three-dimensional tooth object having a root.

The ideal rotation of the teeth is calculated for the individual patient.

To aid an operator in interactively determining, with a computer, the setup of the patient's teeth, Bezier curves are provided with handles to allow the operator to manipulate arch shaped tooth arrangements.

Extractions can be selected and software used to calculate a setup with the extracted teeth removed.

A database is maintained, accessible by a computer, and containing data related to each of a plurality of orthodontic practitioners, including default instructions from different practitioners that will apply unless specifically modified by the practitioner in the prescription or instructions.

Data files of scanned shapes maybe pruned to optimize processing, and solid impressions and models may be manicured and trimmed to optimize data input.

Points can be interactively selected by an operator to define an occlusal plane and to create representations of individual teeth that include a mid-developmental lobe plane.

Modifications to a computer determined setup can be made by an operator. The operator has the ability to make small translational modifications in the mandibular lobe plane of a tooth and to make rotational modifications about the long axis of a tooth. After each and every individual modification, arch setup is recalculated to obey the rules laid out for the occlusion.

An archwire may be designed to satisfy various conditions, including wire symmetry, wire lying in an archwire plane, wire perpendicular to each tooth's mid-developmental lobe plane (MDL.Pl), wire passing through the body of each bracket, the location in the bracket not at extremes, aesthetic wire cure, a minimum number and magnitude of inflections, or slight bends, in the wire, preferably with bends confined to an archwire plane allowed with higher order bends disallowed.

Modifications may be made by an operator to an appliance design. The operator may override and adjust a computer calculated position and configuration of appliances. An operator is typically a skilled person at an appliance manufacturing facility, but can also be a treating orthodontic practitioner. After each and every adjustment, the appliance setup is recalculated to accommodate each specific change, so that the immediate results of each change are immediately apparent to the user or practitioner.

Slot cutting parameters, where brackets are being made, can be made to follow certain rules by routines in a computer. Slot depth minimums and maximums should avoid protrusions and maintain bracket strength.

Buccal tubes can be formed by cutting components thereof from bracket blank material. A "lid", for example, may be secured over a slot to form an enclosed tube.

These and other features, objectives and advantages of the invention are set forth in the following detailed description of the drawings, in which:

BRIEF DESCRIPTION OF THE DRAWINGS

FIGS. 35Y-35CC are diagrams illustrating relative positioning and orientations of teeth in a setup determination where extractions are considered.

FIG. 35DD is a diagram illustrating alternative tooth identification schemes.

FIGS. 41-42A and 42B are diagrams illustrating slot cutting in brackets.

DETAILED DESCRIPTION

Figure 1:
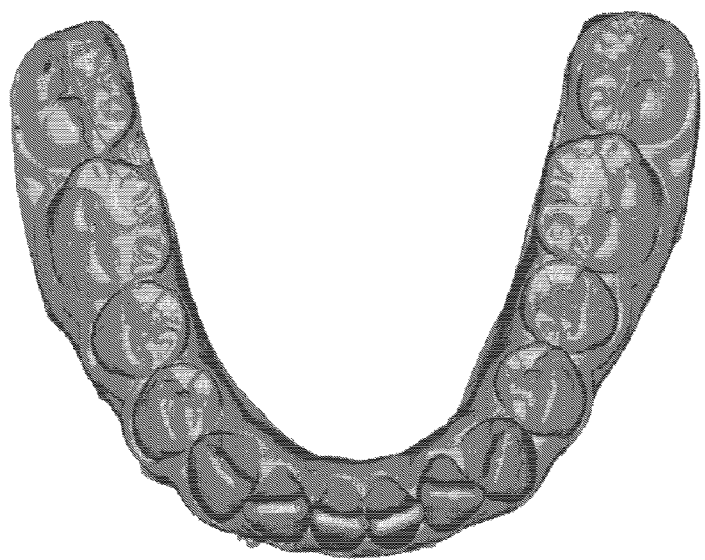
FIG. 1 is a computer screen illustration displaying a mandibular computer model in an occlusal view from the scanned 3D image of the patient's lower arch.

The present invention is described in its preferred embodiments, which relate to orthodontic systems of the types referred to, for example, in U.S. Pat. No. 5,431,562 and Published International patent application No. PCT/US00/35558, both hereby expressly incorporated herein by reference. The invention includes components of such systems usable for generating digital models of a patient's teeth, for determining dental related anatomy and treatment plans, for generating setups of patient's teeth to be achieved by treatment plans and for designing, selecting and/or manufacturing orthodontic appliances to carry out treatment plans.

This description is divided into twelve sections, each relating to subject matter of inventions set forth herein. These sections are grouped into three parts, corresponding to respective portions of the system and method to which they relate. The inventive concepts set forth herein, to the extent not claimed herein, may be claimed in continuing or divisional applications.

The first part of this description deals with the generation of digital information of the patient's dental related anatomy for use by a computer aided system that will be used for arriving at a setup of the teeth to be achieved during treatment and for the determination of a design for an orthodontic appliance that will be used to achieve the treatment. This first part is in the form of an interactive system by which a user refines or simplifies three dimensional data of the patient for subsequent processing. The interactive system allows the skill of the user to supplement the efficiency of the computer in preparing the data. Such a user may be a treating orthodontic practitioner, but a skilled operator at an appliance providing facility or data processing facility is more likely more suitable for operating this part of the system.

The second part of the description relates to an interactive computer sub-system for generating a digital model of and displaying a desirable treatment goal. In particular, a final arrangement of a patient's teeth is calculated and displayed. This part of the system operates interactively with a user having orthodontic skill making selections and modifications to achieve a desirable treatment result. The user is, in the first instance, preferably a skilled operator at an appliance providing facility or a data processing facility. Alternatively, in the first instance, the calculation of a tooth setup may be entirely automatic. After an initial setup is calculated for the patient's teeth, an orthodontic practitioner or treating professional may provide further input or review and may make modifications to the setup or treatment plan.

The third part of the description relates to the designing of an appliance to carry out the treatment plan or achieve the calculated setup. This part may also be interactive, with a user being an operator at an appliance providing or data processing facility or being an orthodontic practitioner or treating professional, or a combination of the two.

Interactive use of the components of the system may be carried out on a computer located at the user's location and running software embodying the system, or remotely on a server. In one embodiment, the software is run on a server at an appliance-providing facility or a data processing facility, with portions that are used interactively by a treating professional or orthodontic practitioner or other person being accessed remotely, preferably via the internet, using a standard browser, which may or may not be supplemented with plugins, or using other local software routines.

PART ONE

Determining the Shape of the Dental Arch and Generating Three-Dimensional Tooth Objects Providing orthodontic treatment with an appliance that is suitable for an individual patient involves the collection of anatomical and other personal information of the patient, the preparation of the information in a form that can be usefully processed to determine a treatment plan and the properties of an appliance for carrying out the treatment plan, the processing of that information, and the use of the information in making the appliance. The quality of the information acquired by the system affects the quality of all of the steps that follow.

I. Patient Input

A digital file or a folder or other plurality of files is maintained on one or more computers, preferably on a server located at an orthodontic appliance custom design determining facility. The file or files contain information regarding individual patients, their treating practitioners and their treatment plans. The information may be maintained, for example, in related database files. A file of records of doctors who are the customers of the facility may contain information identifying the doctor by name and an assigned customer number that is created when the doctor becomes a customer. Such file might be linked to or contain information relating to default preferences of the doctor as to prescriptions and appliance hardware. A file of records of patients of the doctors may contain information with links to the doctor records identifying the patient and an assigned patient number that is created when the patient case is opened by the doctor with the facility. Such files might be linked to various files of other information relating to patients, the patient anatomy, patient medical history, the treatment plan and ultimately the treatment goal, and to data correlated to appliances proposed for the treatment that are the result of other work performed at the facility.

The patient information may be communicated by the doctor to the facility along with prescription information, any lateral cephalograms, tracings or x-rays of the dental or skeletal anatomy of the patient, any photographs or other images of soft tissue of the patient. All such information is preferably maintained at the facility in digital files that are linked to the respective patient records in the patient's files. If digital scan data of the patient's teeth have been obtained by the doctor or patient, that scan data may be transmitted in digital form and maintained at the facility with the other digital information of the patient. In a system described below, impressions of a patient's teeth, or casts made from an impression, are provided by the doctor to the facility. These impressions include upper and lower arch impressions of the teeth of the patient in their maloccluded, or pretreatment, state. When case information is received by the facility, a workorder number is assigned.

II. Scanning

Scanning is a general term used here to describe the generation of digital data of the anatomy of a patient, and typically includes data of the shapes of the teeth of the patient. Preferably, the scanning results in a file in the form of a point cloud for each of the arches. The data may be produced directly from the patient's mouth or from a model or impression of the patient's mouth. For subsequent phases in the operation of the system, it does not matter how the data is generated, as long as it is in a form that can be understood by the equipment or converted to a form that can be used by the equipment. Some scanning methods that are acceptable are those described in U.S. Pat. No. 5,431,562 and in Published International Patent Application No. PCT/US00/35558, both hereby expressly incorporated herein by reference. Other methods already known in the art or yet to be developed may also be acceptable.

One method of scanning the patient's teeth at a facility that receives an impression of the teeth from the doctor may start with pouring a stone model or plaster cast for each of the maxillary and mandibular impressions. Two models of each are preferably made, particularly where a destructive scanning method is used. The models are labeled and identified with the work order number of the case.

One set of the models is then manicured to remove or smooth features on the surface of the model that can result in data artifacts when the models are scanned. The models are trimmed to minimize amount of unnecessary data that will be generated by the scan to keep scanning and processing time at a minimum.

A destructive scanning process may be used in which the manicured set of models is coated to minimize contrast bleed into the plaster of the model, which is typically white. 404 epoxy paint, for example, is mixed and the model is coated with it. The coated models are arranged on a tray, and urethane is mixed and poured over the model, and vacuum is applied and the urethane is cured, encasing the model in the urethane.

A destructive scan of the encased model is carried out with the mass milled or shaved in layers of 0.00.times. inches until the coating is first exposed. With each successive shaving of the mass, the boundary is progressively exposed, with inflections in the model surface and undercuts being fully captured by the boundary that is revealed by the scan, where x represents the resolution desired, here indicated as some thousandths of an inch With each pass of the mill optical equipment is used to digitize the coordinates of points on the boundary to whatever resolution is deemed desirable. For the production of reliable appliance placement jigs, for example, as high a resolution as is practical is desirable, with a minimum resolution being in the range of 100 to 150 points per inch. The points defining each arch are saved as pointcloud file, which is identified with the workorder number of the case.

III. Validation of Data, Individualization of Teeth and Determination of Landmarks Point cloud data, however it is derived, is converted into STL formatted files that contain polygon mesh objects. The data is validated to insure that the data is meaningful and the file is pruned to remove excess or unnecessary information. Each of the teeth is isolated as a discrete tooth object One copy of the data defining each individual tooth is saved with a portion of adjacent teeth, which is useful for certain purposes such as positioning appliances on the teeth when in their initial maloccluded state. Another and working set of data isolates each tooth as a watertight volume, with gingival excess trimmed and adjacent teeth separated from it. This may be achieved automatically, interactively with an operator directing the operations on a monitor, or with a combination of operator and software actions. Processing the data automatically using feature recognition software to isolate tooth objects then displaying the automatically generated result to an operator to resolve ambiguities or errors and to verify the results provides an optimal combination of speed and accuracy.

Minor object repairs may similarly be made to remove artifacts, which may include modifying of tooth crown shapes in the data to eliminate jig fit interferences. This is presently accomplished most efficiently by an operator on a computer screen with the aid of software tools. This process may involve selecting, then elevating, lowering and smoothing areas that could cause poor jig adaptation, for example. This assures that bracket positioning jigs that are custom made with a custom orthodontic appliance will accurately position the appliances on the patient's teeth.

The data of the objects representing each of the teeth may then be intelligently decimated, with data of unnecessary resolution thinned to make the operations more efficient. The areas that are to be contacted by the jigs are, however, more critical than other areas so that these areas are maintained at higher resolution than other portions of the tooth crowns. Each of the tooth objects is saved by FDI nomenclature and work order number (e.g. Workorder#RAW42).

Once the individual tooth objects are created in three-dimensional processable data, selected parameters or properties of the patient's dental anatomy are identified or calculated for use in determining a virtual setup or the desired finish positions of the teeth. These parameters and properties simplify the data for calculation and include the geometric references that can be used by software algorithms to develop a setup or occlusion.

IV. Defining the Mandibular Trough

Figure 2:
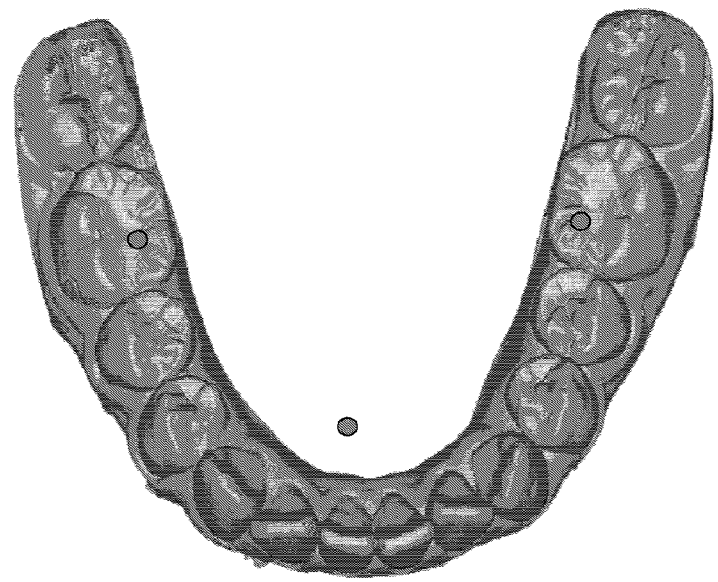
FIG. 2 is a computer screen illustration displaying point selection for determination of an occlusal plane.
Figure 3:
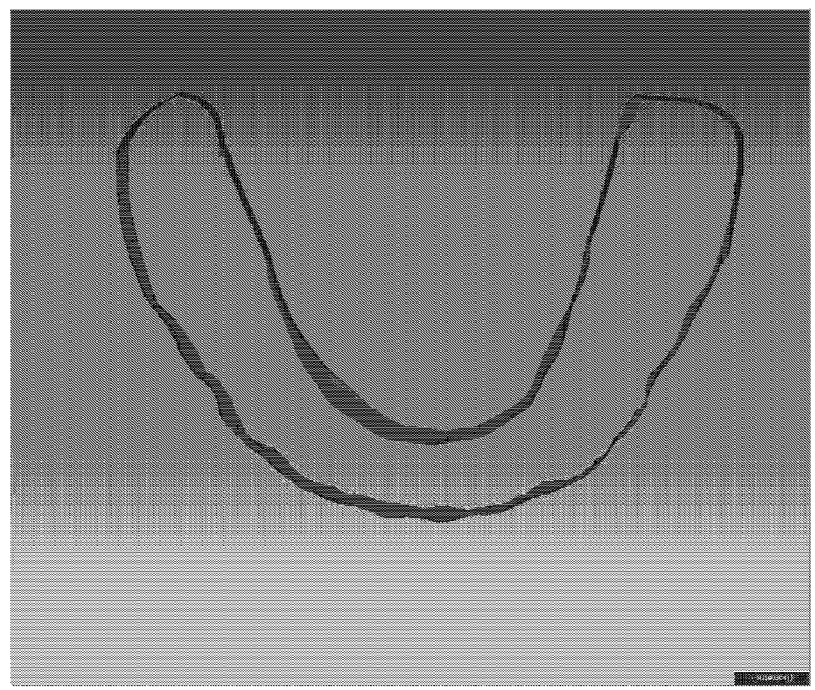
FIG. 3-6 are computer screen illustrations displaying steps in determining a mandibular trough curve.

The shape of the trough within the rigid mandible that contains the roots of the mandibular teeth defines an archform that constitutes a significant constraint on the positioning of the teeth. Definition of this trough mathematically can be accomplished from the scanned or photographic or other data of the patient's lower dental arch This may be achieved interactively by an operator bringing the mandibular computer model to the screen in an occlusal view from the scanned 3D image of the patient's lower arch. (FIG. 1.) The occlusal plane is derived by identifying three points that include the mesial buccal cusps of the first mandibular molars and the incisal tip of one of the mandibular centrals. (FIG. 2.) These three points can be quickly and accurately selected by an operator on the occlusal view on the computer screen, although pattern recognition software can be used.

Figure 4:
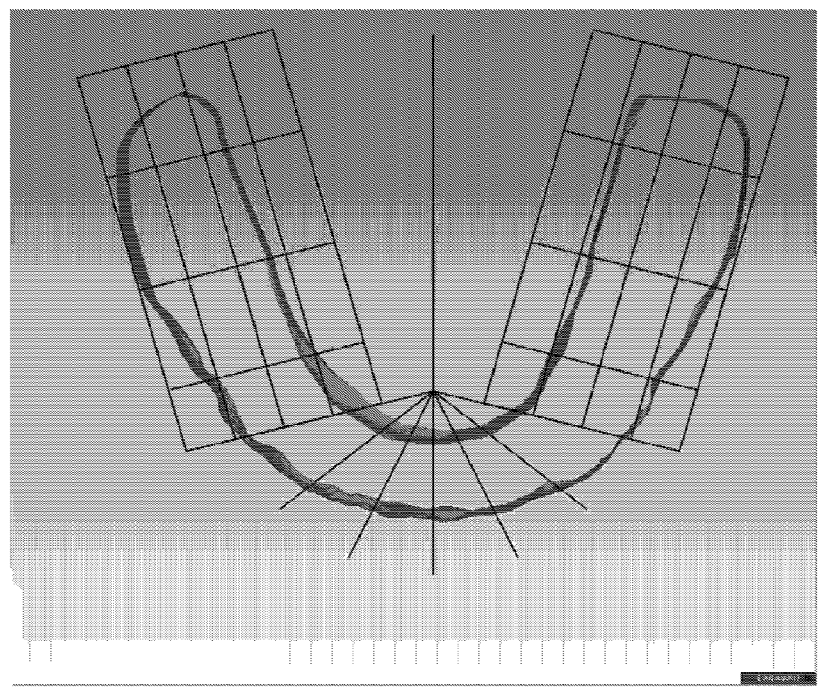
Figure 5:
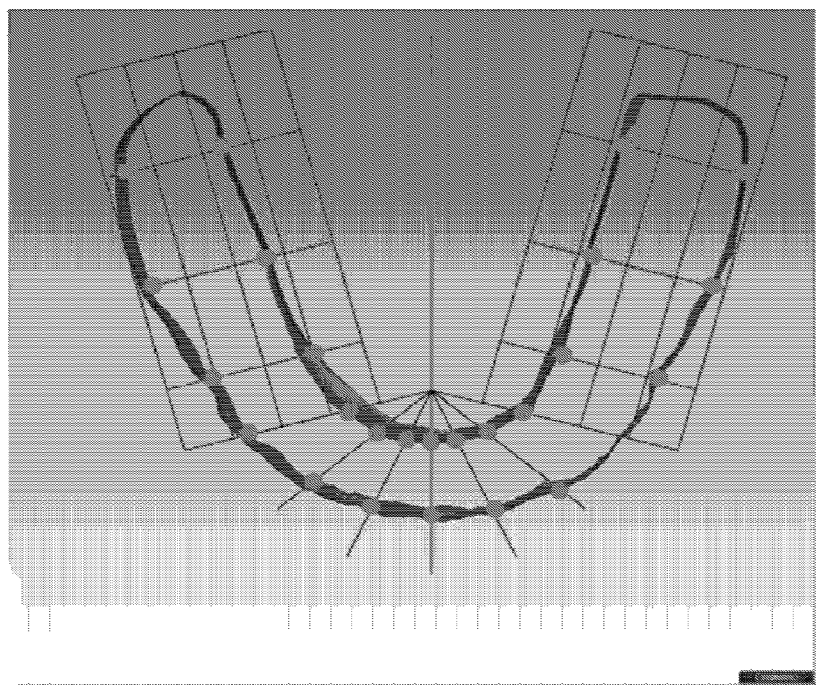

The image is rotated so that occlusal plane (O.pl), so defined, is set parallel to screen and so that the arch is symmetrical about a vertical center line with the anterior teeth at the bottom of the screen. A section is made through the data below the teeth. A symmetrical grid is laid over the section and intersections of the grid with the data are selected. (FIG. 4.) The selection may be done automatically or by an operator on the screen. The points define the facial and lingual boundaries of the mandibular trough. (FIG. 5.)

Figure 6:
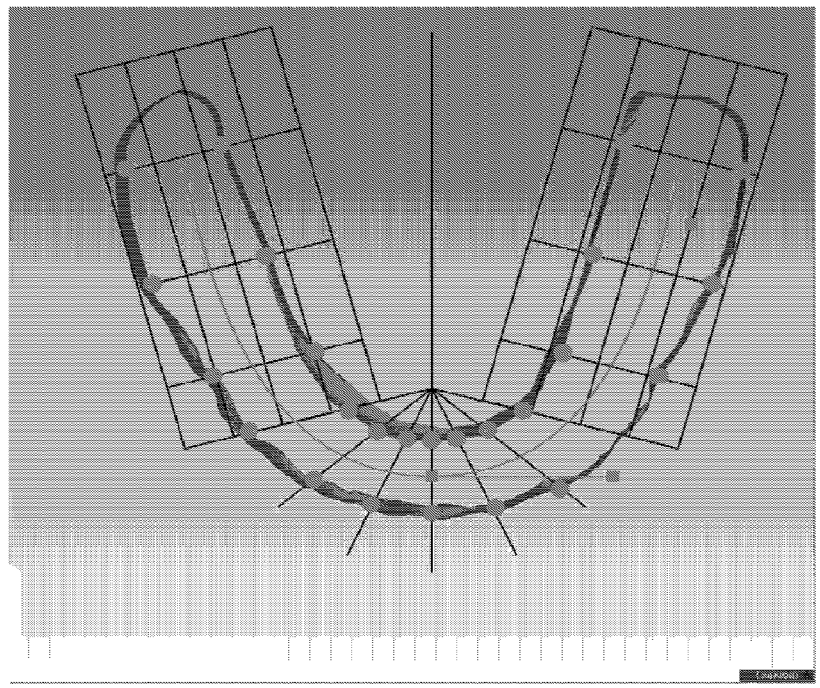

A smooth symmetrical bezier curve is calculated through the midpoints of the grid lines that intersect the trough. (FIG. 6.) Handles at the midline and at the distal ends of the curve allow the operator to control the shape of the bezier curves so that the curve generally follows the midline of the trough between the midpoints. The mandibular trough curve (MT.cv) and the orientation of the occlusal plane provide the reference for the orientation of the individual tooth objects in the setup of the occlusion.

V. Landmark Identification

For lower incisors and first bicuspids, the mid-developmental lobe plane and the crown long axis are defined. This may be carried out by an operator bringing each tooth object to the screen individually as a 3-D object and selecting certain points, using software tools to make calculations. Pattern recognition software can be used for this purpose or to simplify the operators tasks, to aid the operator in selections, or to improve the accuracy of operator selections.

Figure 7:
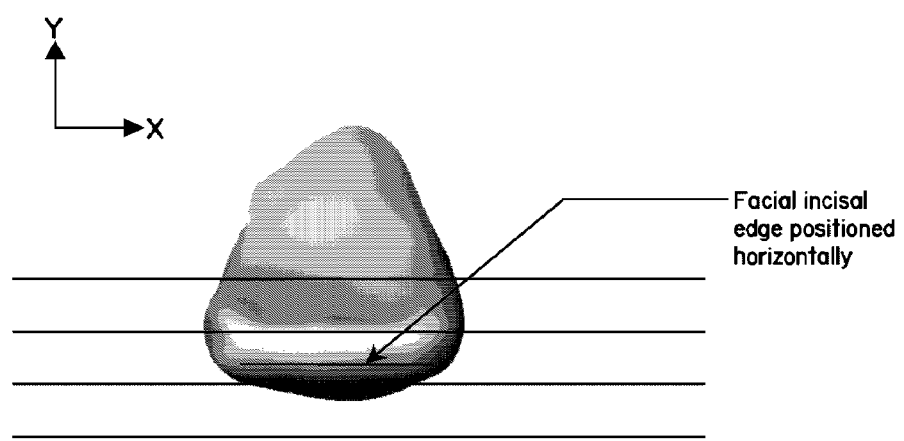
FIGS. 7-32 are computer screen illustrations displaying steps in the selection of tooth landmarks.
Figure 8:
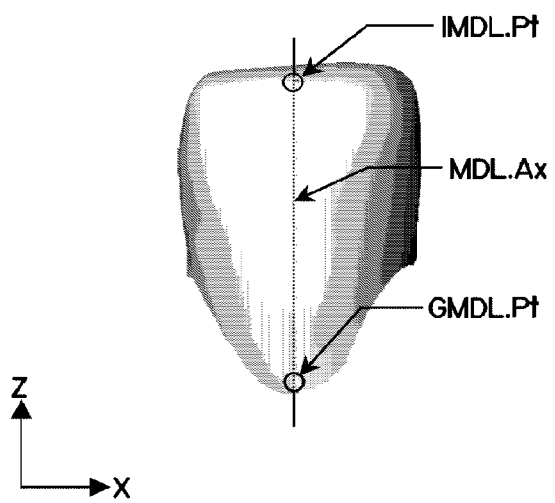
Figure 9:
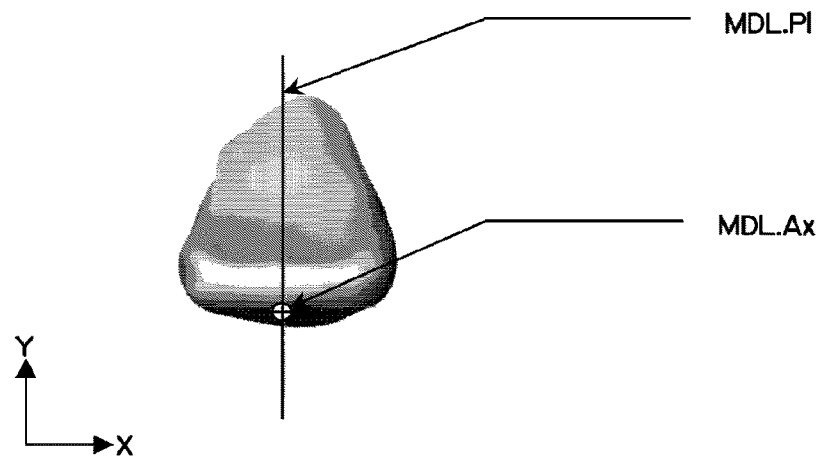

Each of the tooth objects may be brought to the screen and viewed from the incisal side. (FIG. 7.) For reference, the facial side is facing down and the facial-incisal edge is oriented horizontally on the screen, or parallel to the X axis. Then the tooth is rolled upward 90.degree. showing an enface view of facial surface. With the facial surface of tooth presented to the operator, the mid-developmental lobe axis (MDL.Ax) is identified by selection of its extents incisally (MDL.Pt) and gingivally (GMDL.Pt). (FIG. 8.) Then the object is rotated on the screen to present an incisal view and bring MDL.Ax perpendicular to the XY plane and the incisal edge parallel to X-axis, and a vertical mid-developmental lobe plane (MDL.Pl) is defined through MDL.Ax and perpendicular to the X-axis, which can be used to represent the tooth (FIG. 9.) While these steps can be carried out by an operator, they can be executed in background without screen display of the steps.

Figure 10:
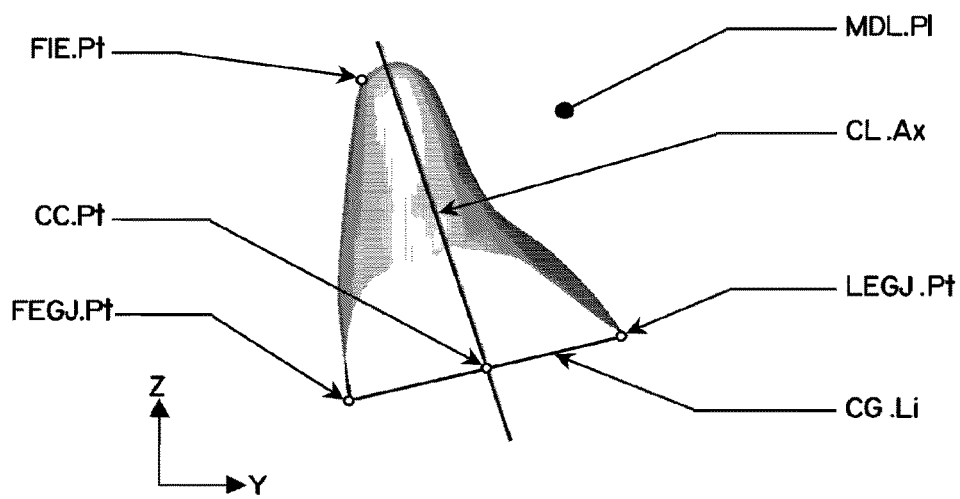

In a cross-section view of each tooth represented by MDL.Pl, a lingual-enamel-gingival junction is identified that defines lingual-enamel-gingival junction point (LEGJ.Pt). (FIG. 10.) Also in this plane, a facial-enamel-gingival junction is identified that defines the facial-enamel-gingival junction point (FEGJ.Pt). Points LEGJ.Pt and FEGJ.Pt define a crown-gingival line segment (CG.Li), the midpoint of which can be calculated as the cervical-center-point (CC.Pt) of the tooth. The mid-developmental lobe plane can be used to define, at least initially, mesial-distal positioning of a bracket on the tooth.

In mid-developmental lobe plane (MDL.Pl) line segment through cervical-center-point (CC.Pt) can be calculated that extends incisally above tooth, which is achieved most easily by an operator visually moving the unconstrained end of the line to the center of body of incisal edge of the tooth. This line defines the crown long axis (CL.Ax) of the tooth. Also, the facial incisal edge point (FIE.Pt) can be selected by the operator. For mandibular anterior teeth, point FIE.Pt is typically forward of the CL.Ax and indicates where the tooth contacts a tooth of the upper arch.

Figure 11:
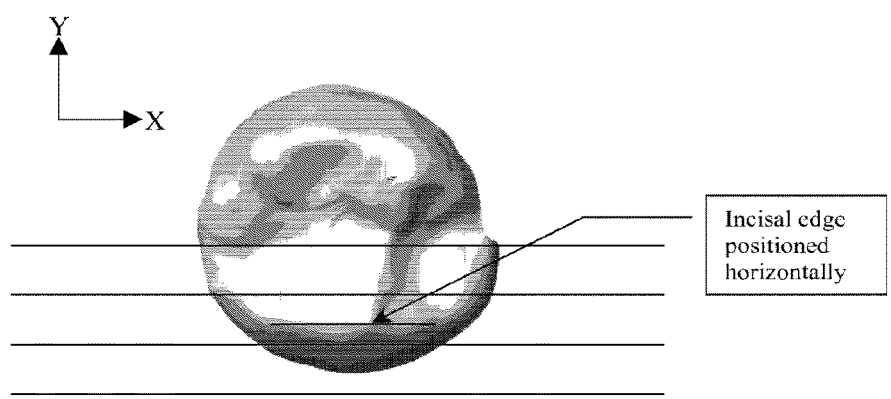
Figure 12:
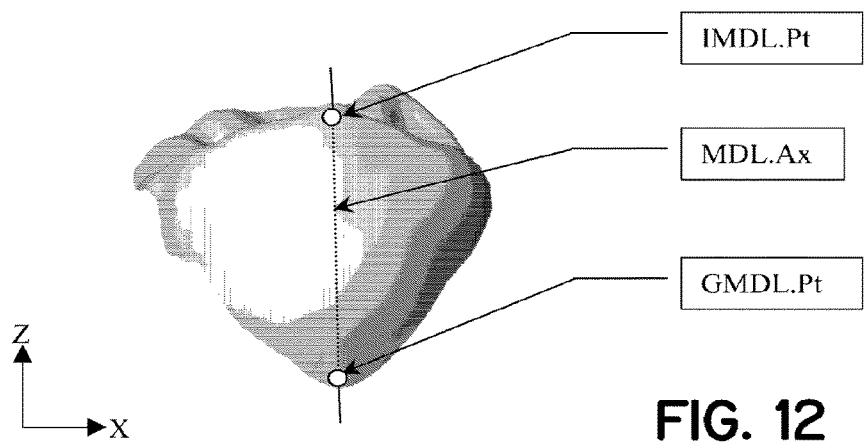

For lower second bicuspids, each tooth is brought to the screen individually as a 3-D object that is rotatable, panable and zoomable. The mid-developmental lobe and the crown long axis of the tooth are defined by viewing the tooth incisally on the screen with the facial side down and the incisal edge parallel to the horizontal or X-axis (FIG. 11), then rotated upward 90.degree. to show an enface view of the facial surface of the tooth (FIG. 12). With the facial surface of the tooth presented to an operator, the mid-developmental lobe axis (MDL.Ax) may be identified by selection of extents incisally (IMDL.Pt) and gingivally (GMDL.Pt). Then, with the tooth rotated again to be viewed from the incisal or occlusal side so that the MDL.Ax perpendicular to the XY-plane and the incisal edge is parallel to the X-axis, a vertical plane is positioned through MDL.Ax, which is defined as the mid-developmental lobe plane (MDL.Pl) (FIG. 12). This plane may define the initial mesial-distal positioning of an appliance.

Figure 13:
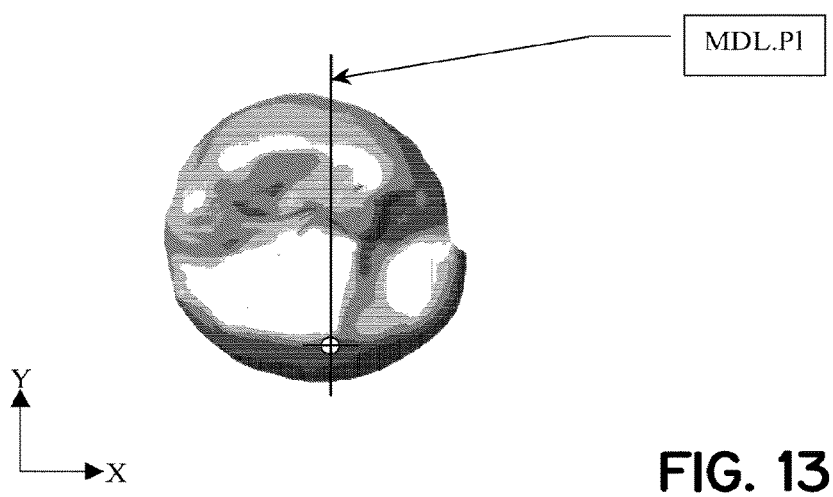
Figure 14:
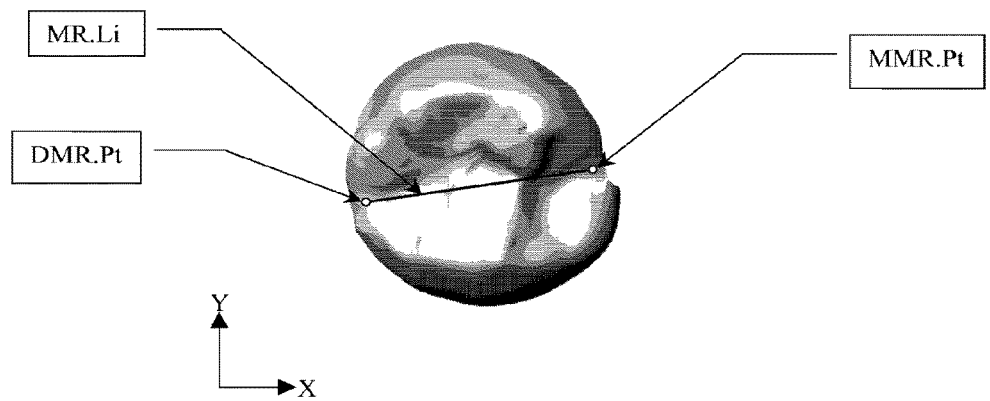

With MDL.Ax still perpendicular to the XY-plane and the incisal edge parallel to X-axis, mesial and distal marginal ridges are identified by selecting points MMR.Pt and DMR.Pt, respectively. (FIG. 13.) A marginal ridge line segment (MR.Li) is defined through points MMR.Pt and DMR.Pt. (FIG. 14.)

Figure 15:
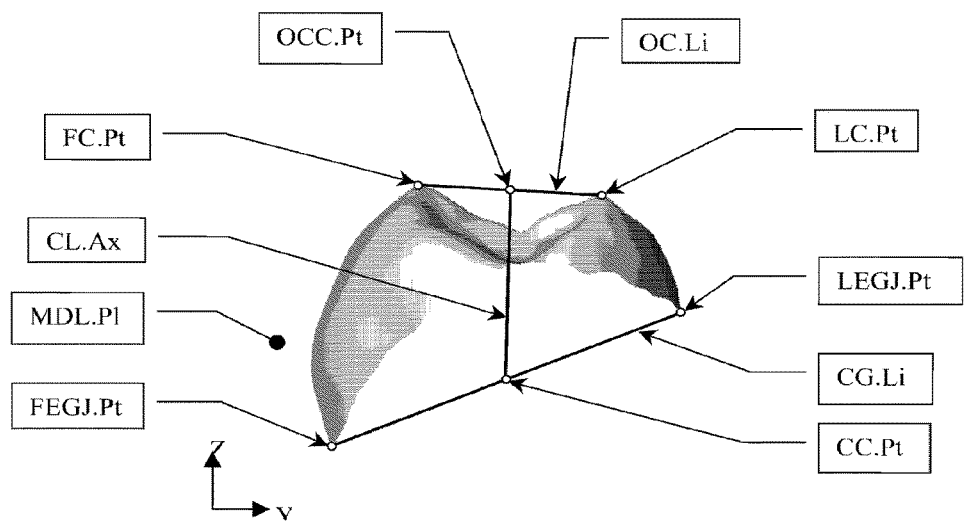

In a cross-section view of the tooth created on the screen along plane MDL.Pl, a lingual-enamel-gingival junction is identified that defines the lingual-enamel-gingival junction point (LEGJ.Pt) and a facial-enamel-gingival junction is identified that defines the facial-enamel-gingival junction point (FEGJ.Pt). (FIG. 15.) Points LEGJ.Pt and FEGJ.Pt define a crown-gingival line segment (CG.Li). The midpoint of line segment CG.Li is calculated as the cervical-center-point (CC.Pt). A lingual cusp point (LC.Pt) and facial cusp point (FC.Pt) are selected. Points LC.Pt and FC.Pt define an occlusal cusp line segment (OC.Li). The midpoint of OC.Li is calculated as the occlusal-cusp-center-point (OCC.Pt). A line segment through CC.Pt and OCC.Pt defines crown long axis (CL.Ax) of these bicuspids. (FIG. 15.)

Figure 16:
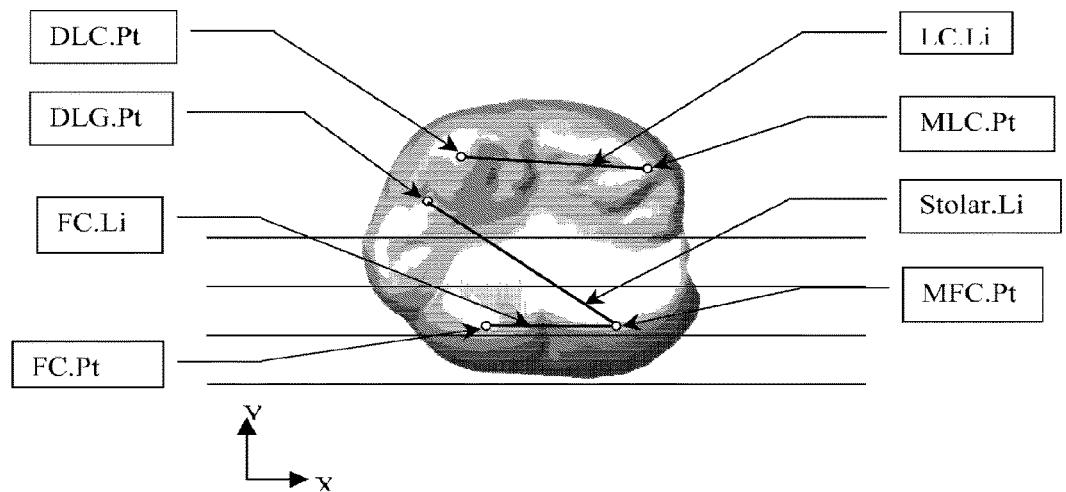

For lower molars, each tooth may also be brought to the screen individually as a 3-D object that is rotatable, panable and zoomable. A mid-developmental lobe plane and crown long axis are defined for these molars. The tooth object is viewed from the incisal side with the chord between its mesial-facial and distal-facial cusps parallel to horizontal X-axis and its facial side facing the bottom of the screen (FIG. 16). The operator (or a program) may select the distal-lingual groove point (DLG.Pt), the distal-lingual cusp point (DLC.Pt), the mesial-lingual cusp point (MLC.Pt), the facial cusp point (FC.Pt), and the mesial-facial cusp point (MFC.Pt). Points DLC.Pt and MLC.Pt define the labial cusp line segment (LC.Li). Points FC.Pt and MFC.Pt define the facial cusp line segment (FC.Li). Points DLG.Pt and MFC.Pt define the line segment Stolar.Li used for occluding upper molars.

Figure 17:
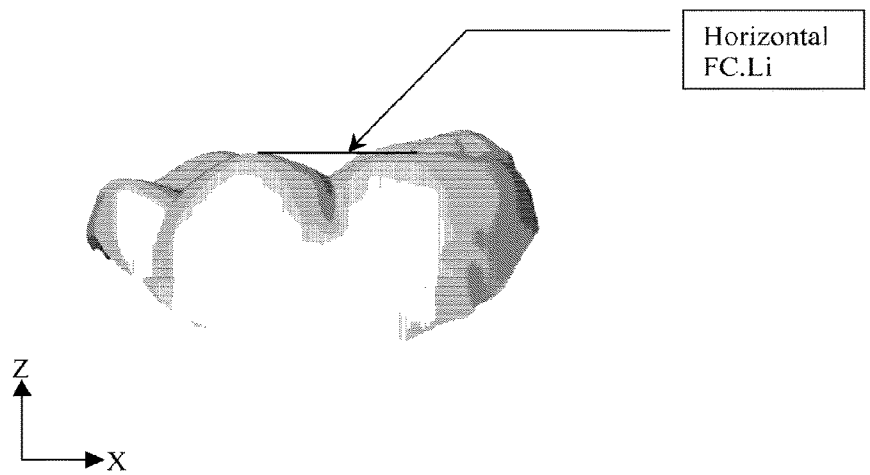
Figure 18:
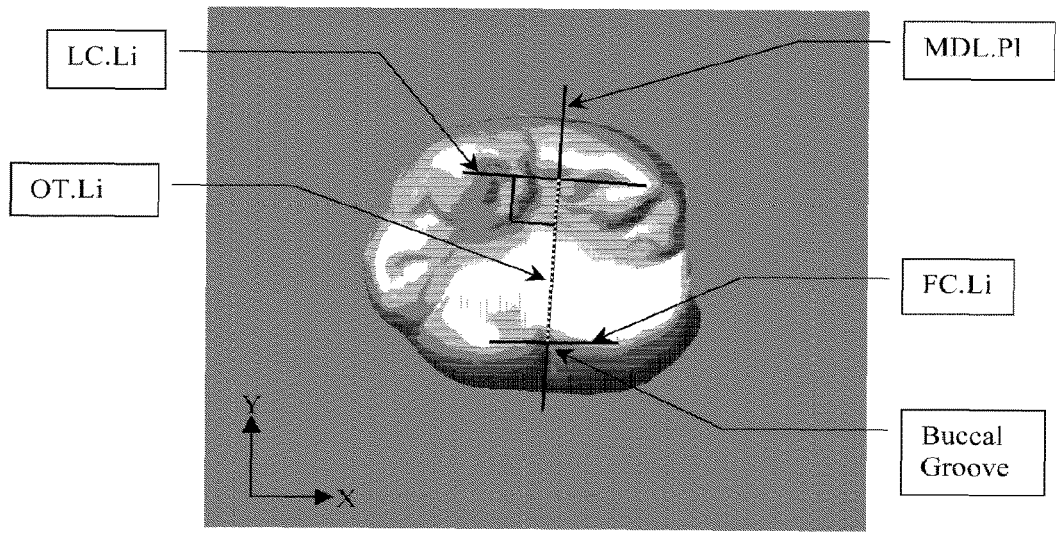

The tooth is rolled upward to show the enface view of facial surface with FC.Li parallel to the X-axis. (FIG. 17.) The image is rotated 90.degree. downward to view incisal surface again. (FIG. 18.) An occlusal table line segment (OT.Li) is defined to be perpendicular to LC.Li, coincident with the buccal groove, and connecting FC.Li to LC.Li. In this view, line OT.Li defines the mid-developmental lobe plane (MDL.Pl), which will be used to define the initial mesial-distal positioning of an appliance on the tooth.

Figure 19:
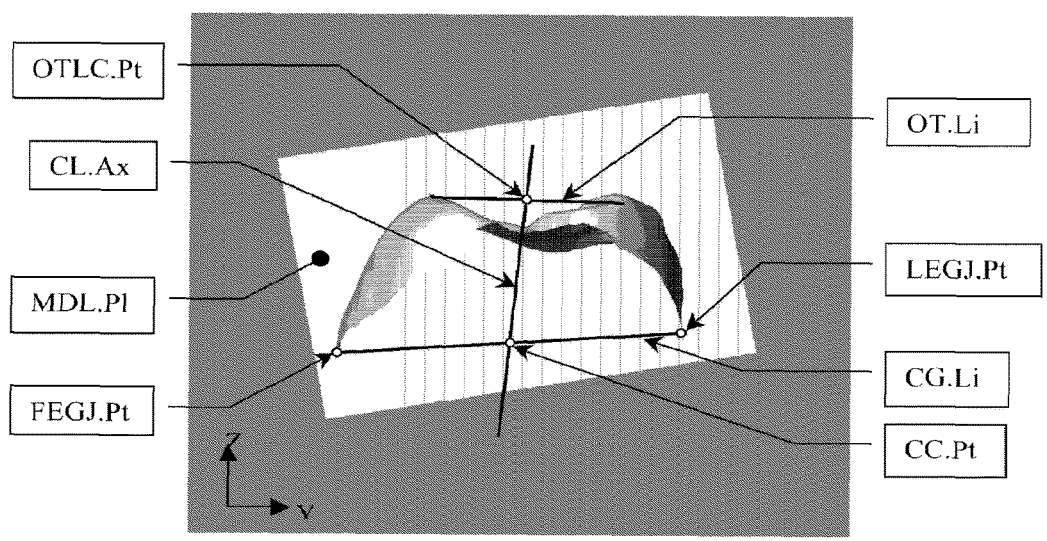

In the cross-section of the tooth along plane MDL.Pl, the lingual-enamel-gingival junction that defines lingual-enamel-gingival junction point (LEGJ.Pt) is selected, and the facial-enamel-gingival junction that defines the facial-enamel-gingival junction point (FEGJ.Pt) is selected. (FIG. 19.) Points LEGJ.Pt and FEGJ.Pt define a crown-gingival line segment (CG.Li). The midpoint, cervical-center-point (CC.Pt), of line segment CG.Li is calculated. The midpoint of OT.Li is also calculated as occlusal table line center-point (OTLC.Pt). A line through CC.Pt and OTLC.Pt defines the crown long axis (CL.Ax) of the tooth.

Figure 20:
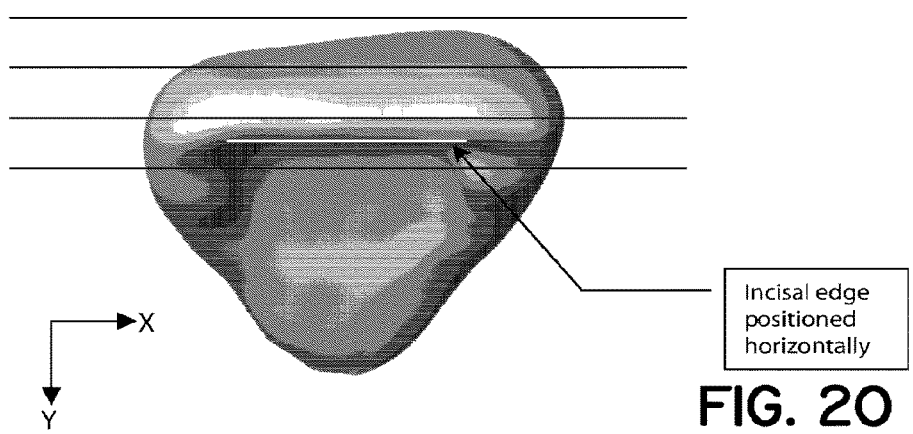
Figure 21:
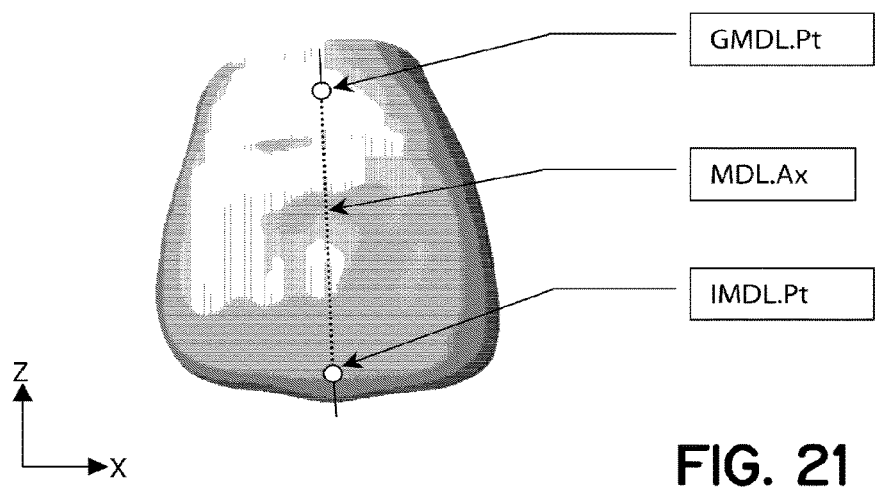

For upper incisors, the tooth 3-D objects are individually brought to full screen rotatable, panable, zoomable images. The mid-developmental lobe plane and crown long axis are defined. With the tooth viewed from its incisal side with its incisal edge parallel to X-axis and its lingual surface facing the bottom of the screen (FIG. 20), the tooth is rolled downward 90.degree. showing an enface view of facial surface of the tooth. With the facial surface of the tooth presented, the operator identifies the mid-developmental lobe axis (MDL.Ax) by selecting its extents, incisal (IMDL.Pt) and gingival (GMDL.Pt). (FIG. 21.)

Figure 22:
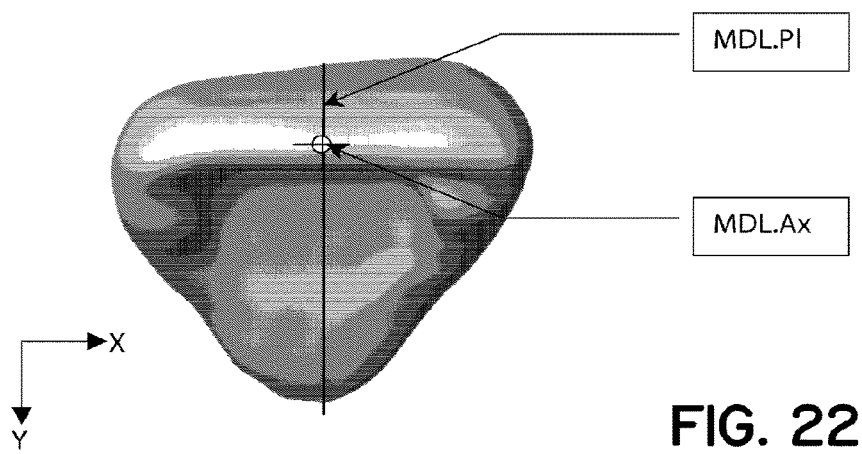
Figure 23:
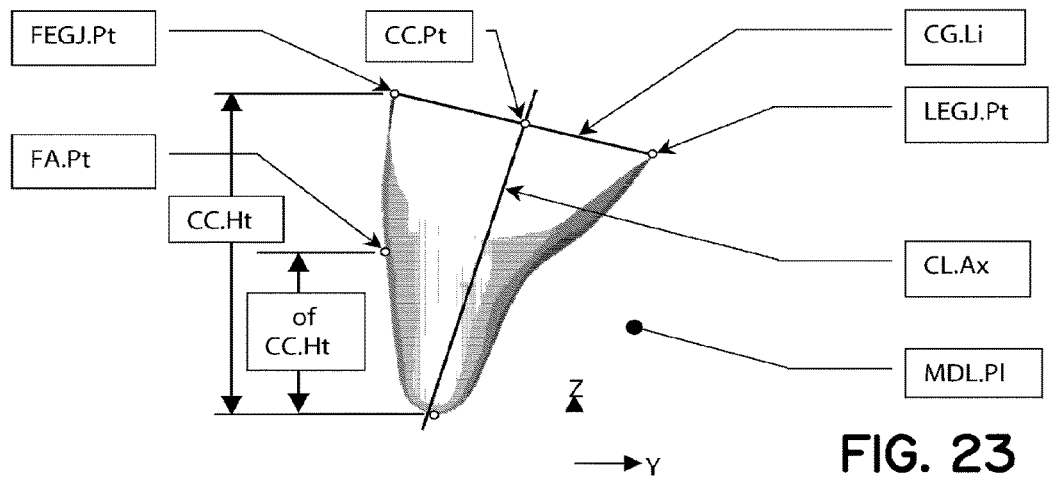

With MDL.Ax rotated perpendicular to XY-plane and the incisal edge to the tooth horizontal or parallel to the X-axis, a vertical plane is positioned through MDL.Ax. (FIG. 22.) This is the mid-developmental lobe plane (MDL.Pl) for this tooth. In a cross-section of the tooth created by MDL.Pl, the lingual-enamel-gingival junction is selected that defines the lingual-enamel-gingival junction point (LEGJ.Pt), and the facial-enamel-gingival junction is selected that defines the facial-enamel-gingival junction point (FEGJ.Pt). (FIG. 23.) Points LEGJ.Pt and FEGJ.Pt define crown-gingival line segment (CG.Li). The midpoint of line segment CG.Li is calculated and defined as the cervical-center-point (CC.Pt). The clinical crown height (CC.Ht) is calculated as the vertical distance from FEGJ.Pt to the most incisal point of the tooth in this view. The facial axis point (FA.Pt) is calculated as one-half of CC.Ht, measured from the most incisal point of the tooth in this view.

The mid-developmental lobe plane may define initial the mesial-distal positioning of appliance. In the mid-developmental lobe plane (MDL.Pl), a line segment is defined through the cervical-center-point (CC.Pt) and extending incisally below tooth. The operator can move the unconstrained end of this line to the center of body of incisal edge of the tooth. This line defines the crown long axis (CL.Ax).

Figure 24:
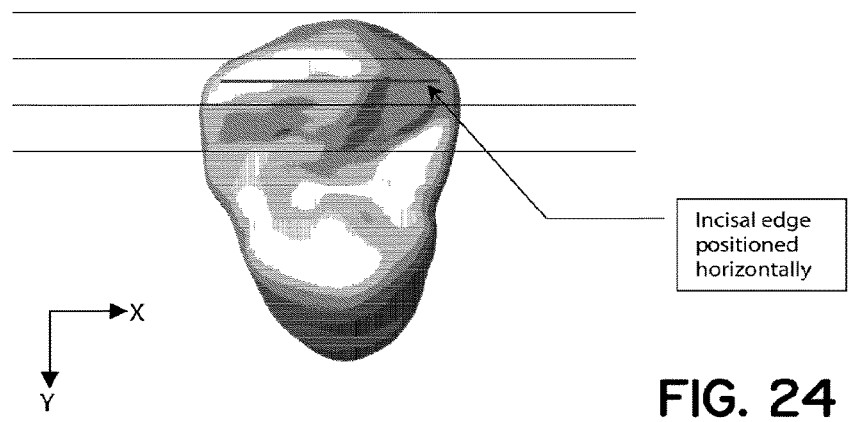
Figure 25:
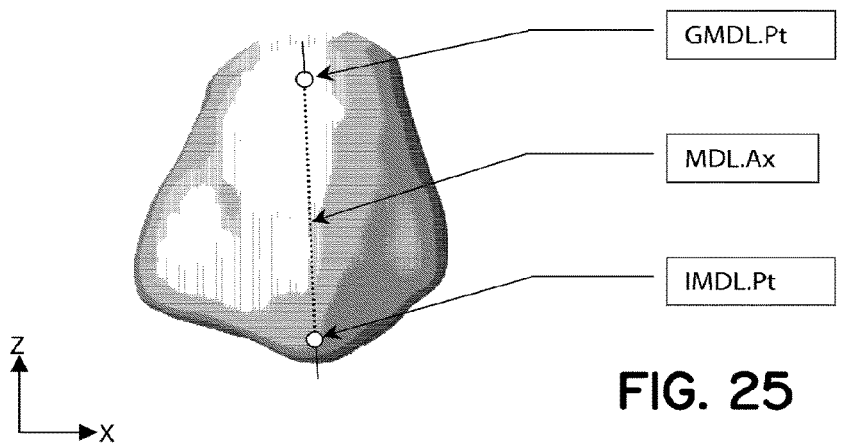

For upper bicuspids, each 3-D object is brought to full screen individually as a rotatable, panable and zoomable object and the mid-developmental lobe and crown long axis are defined. The tooth is viewed from its incisal side with its incisal edge parallel to X-axis and its lingual surface facing the bottom of the screen (FIG. 24). The tooth is rolled downward 90.degree. showing an enface view of the facial surface of the tooth. With the facial surface of the tooth presented, the operator identifies the mid-developmental lobe axis (MDL.Ax) extents incisally (IMDL.Pt) and gingivally (GMDL.Pt) (FIG. 25).

Figure 26:
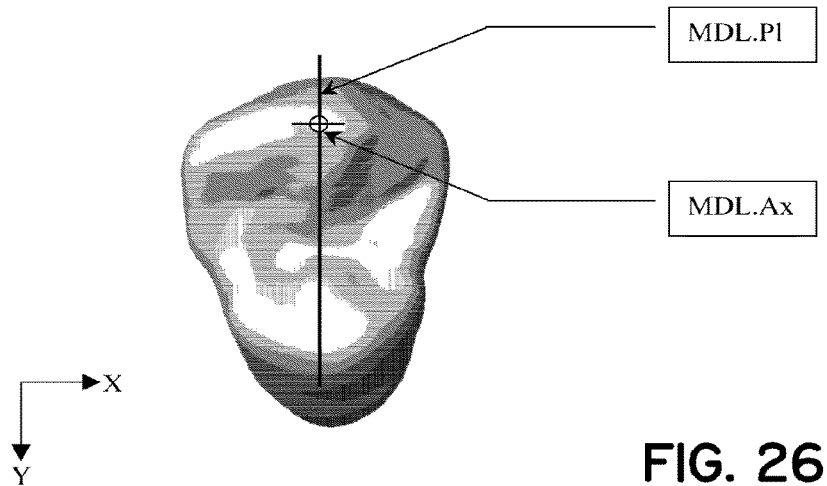
Figure 27:
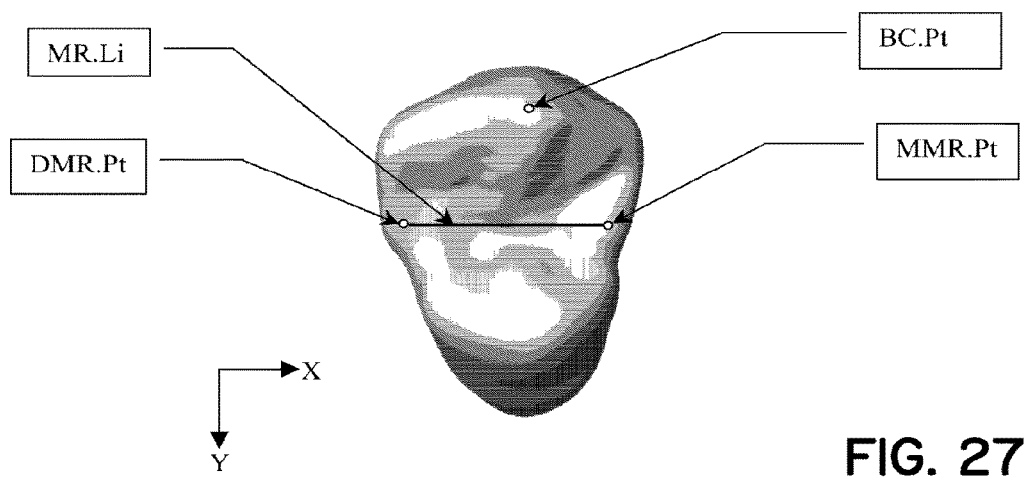

With the image again rotated so MDL.Ax is perpendicular to the XY-plane and the incisal edge is parallel to X-axis, a vertical plane is positioned through MDL.Ax, which defines the mid-developmental lobe plane (MDL.Pl) for this tooth (FIG. 26). This plane will define the initial mesial-distal positioning for an appliance on this tooth. With MDL.Ax perpendicular to XY-plane and the incisal edge of the tooth parallel to X-axis, the operator can select the mesial and distal marginal ridges as points MMR.Pt and DMR.Pt, respectively, and the buccal cusp point (BC.Pt). A marginal ridge line segment (MR.Li) is defined through points MMR.Pt and DMR.Pt (FIG. 27).

Figure 28:
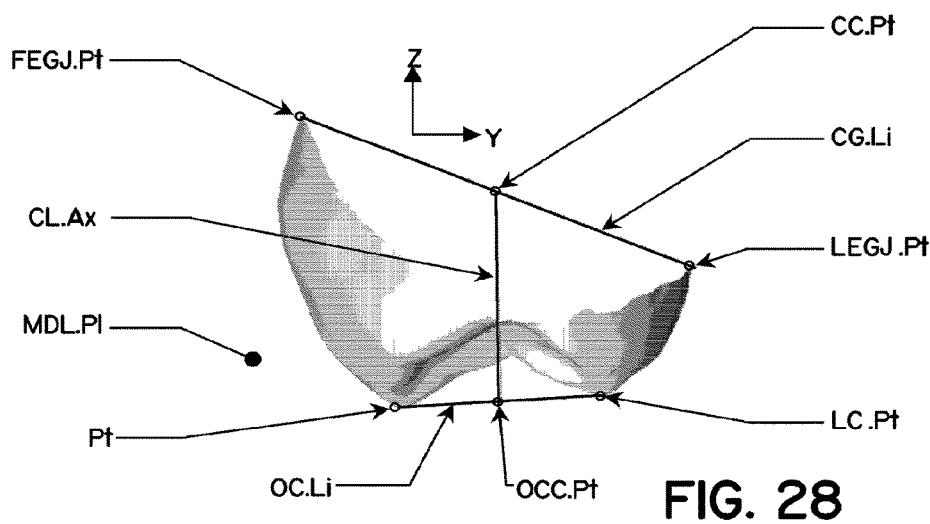

In the cross-section of the tooth created by MDL.Pl (FIG. 28), the lingual-enamel-gingival junction is selected, which defines the lingual-enamel-gingival junction point (LEGJ.Pt) and the facial-enamel-gingival junction is selected, which defines the facial-enamel-gingival junction point (FEGJ.Pt). Points LEGJ.Pt and FEGJ.Pt define a crown-gingival line segment (CG.Li), the midpoint of which is calculated as the cervical-center-point (CC.Pt). The lingual cusp point (LC.Pt) and facial cusp point (FC.Pt) are selected. Points LC.Pt and FC.Pt define occlusal cusp line segment (OC.Li), of which the midpoint is calculated as the occlusal-cusp-center-point (OCC.Pt). A line segment through CC.Pt and OCC.Pt defines the crown long axis (CL.Ax) of this tooth.

Figure 29:
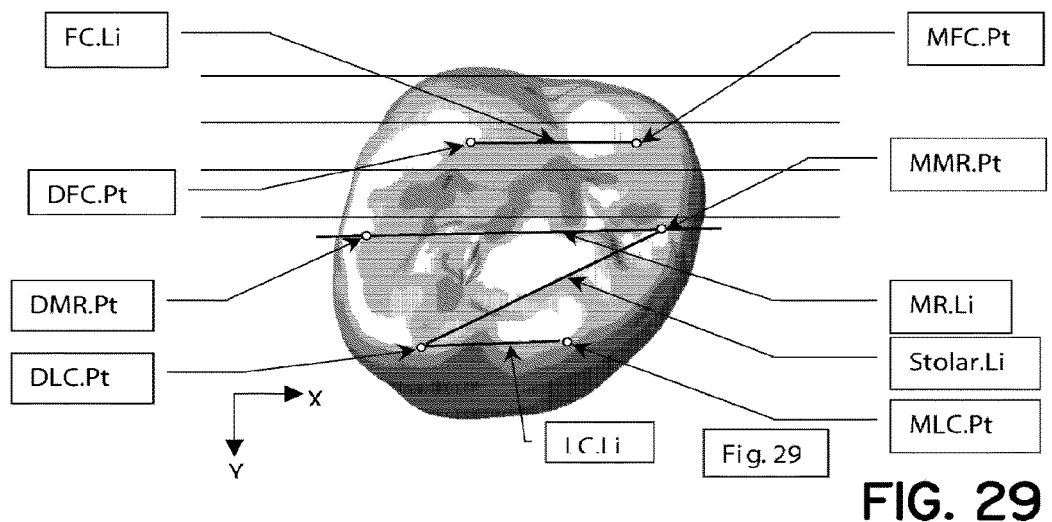

For upper molars, the teeth are brought to full screen as 3-D objects individually rotatable, panable and zoomable. The mid-developmental lobe plane and crown long axis of each are defined. The tooth is viewed from the incisal side with its incisal edge, which is defined as a chord between mesial and distal facial cusps, parallel to XY-plane and lingual surface facing the bottom of the screen. (FIG. 29.) The mesial-lingual cusp point (MLC.Pt), the distal-lingual cusp point (DLC.Pt), the mesial facial cusp point (MFC.Pt), and the distal-facial cusp point (DFC.Pt) are each selected. Points MLC.Pt and DLC.Pt define the labial cusp line segment (LC.Li). Points MFC.Pt and DFC.Pt define the facial cusp line segment (FC.Li). Mesial and distal marginal ridges are selected as points MMR.Pt and DMR.Pt, respectively. A marginal ridge line segment (MR.Li) is defined as that through points MMR.Pt and DMRPt. Points MMR.Pt and DLC.Pt define a line segment Stolar.Li that is used for occluding with lower molars.

Figure 30:
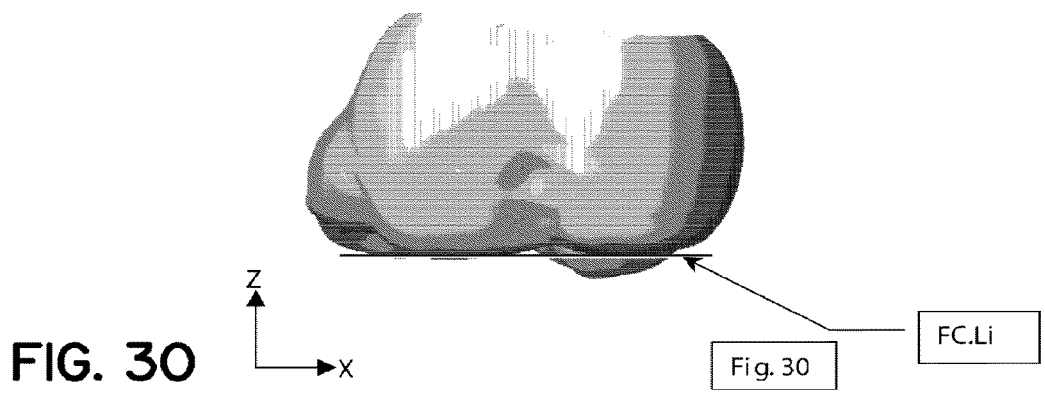
Figure 31:
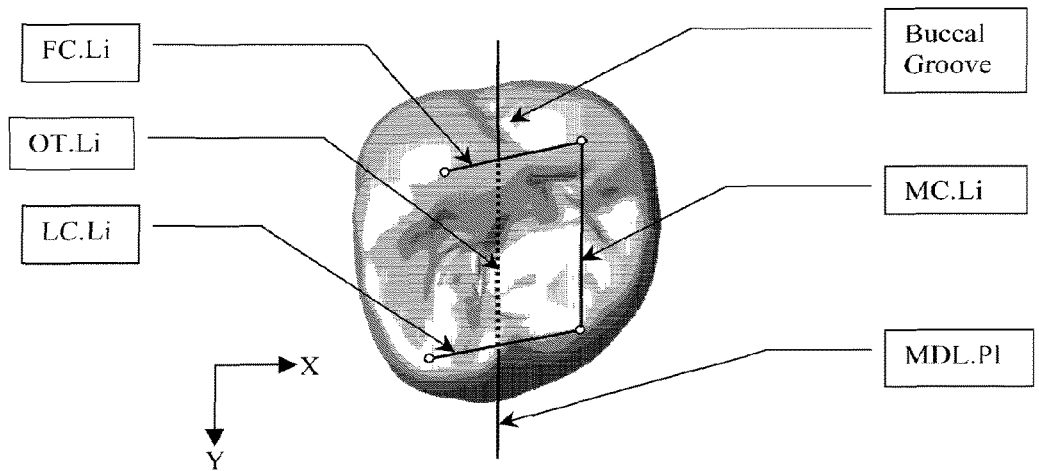

The tooth object is rolled downward to show an enface view of facial surface with FC.Li parallel to the XY-plane (FIG. 30), then rotated 90.degree. upward to view incisal surface again (FIG. 31). Points MFC.Pt and MLC.Pt are selected to define mesial cusp line segment (MC.Li), and occlusal table line segment (OT.Li) is defined to be parallel to line MC.Li coincident with the buccal groove, and connecting FC.Li to LC.Li. In this view, line OT.Li defines the mid-developmental lobe plane (MDL.Pl). This plane will define the initial mesial-distal positioning of the appliance on this tooth.

Figure 32:
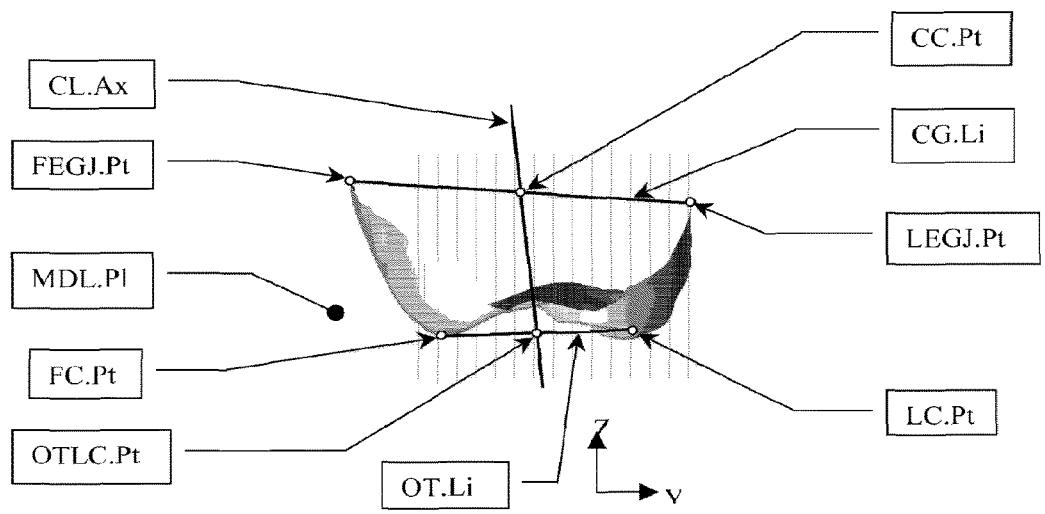

In a cross-section of the tooth created by MDL.Pl, the lingual-enamel-gingival junction is selected, which defines the lingual-enamel-gingival junction point (LEGJ.Pt) and the facial-enamel-gingival junction is selected, which defines the facial-enamel-gingival junction point (FEGJ.Pt) (FIG. 32). Points LEGJ.Pt and FEGJ.Pt define line segment crown-gingival line (CG.Li). The midpoint of line segment CG.Li is calculated as the cervical-center-point (CC.Pt). The midpoint of OT.Li is calculated as the occlusal table line center-point (OTLC.Pt). A line segment through CC.Pt and OTLC.Pt defines the crown long axis (CL.Ax) of this tooth.

VI. Addition of Tooth Roots

Tooth root data can be added to each of the tooth objects from separate files that contain three dimensional data of each of the individual tooth roots. These, separate files can be the result of custom scans of the patient's skeletal anatomy, such as may be generated by various types of X-rays or other equipment. Alternatively, tooth roots may be added from library files that contain three-dimensional shape data of anatomically average or representative tooth roots, or at least of roots that are anatomically average or representative within a group of patients. Library files can be used due to the similarities of root anatomy from patient to patient. Such files are even more useful with modification of the library files with data from the custom scans of the tooth crowns of the patient render can result in the generation of tooth root data that closely approximates the roots of the individual patient.

Even with skeletal data of the patient, modification of patient specific tooth root data using highly accurate tooth crown scans can increase the accuracy of the roots in the resulting digital model. Further, the use of patient specific data, such as X-ray data, combined with general information of tooth anatomy or considered alone, can be intelligently combined with crown scan data without the use of elaborate schemes for directly registering root with crown data taken by different scanning techniques.

Figure 33:
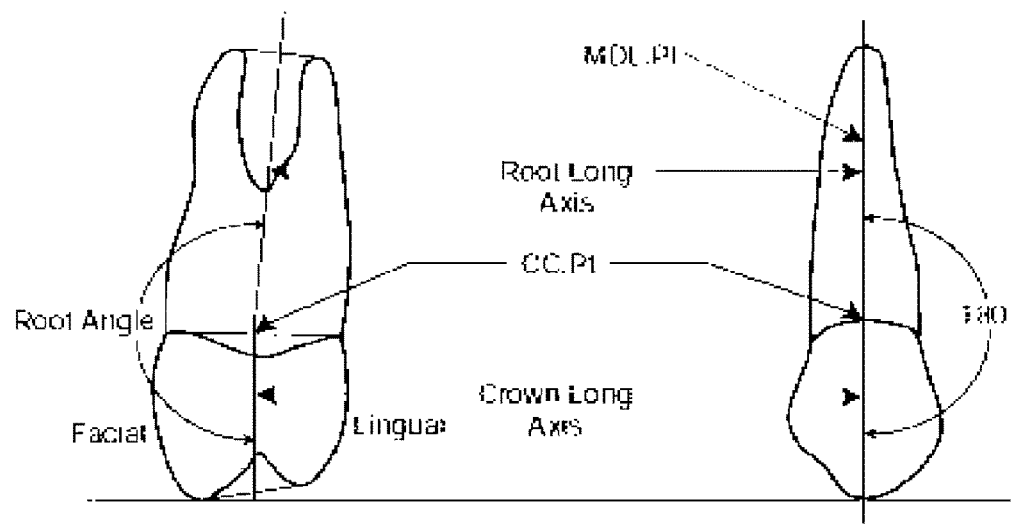
FIGS. 33-34 are diagrams illustrating steps in the addition of tooth root data to tooth representations.
Figure 34:
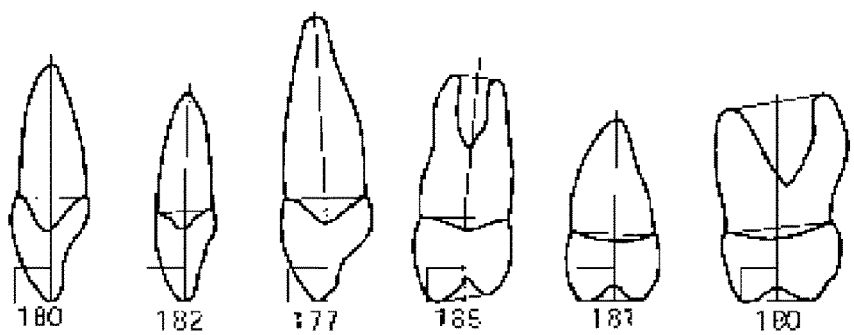
Figure 34:
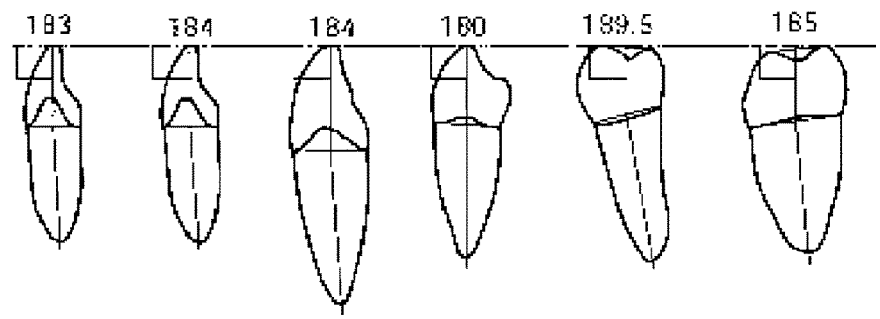

One method of joining the crown and root data to form complete tooth objects is to retrieve the crown shape data produced by the scan and retrieve the root shape data, for example, from a library of root files. Each root image may be retrieved, for example, along with its Root Long Axis (RLA), as illustrated in FIG. 33. If the root data is from a scan of the actual roots of the patient, an analysis may be made to determine and impose an RLA on the tooth root. The CLAs of the crowns and the RLAs of the roots may then be aligned, linking the two tooth parts together. This alignment may be set to a particular relative torque angle, a table of which is illustrated in FIG. 34, which may be retained or modified in the course of determining a tooth set-up.

One way of customizing tooth root data is to start with root image files and representing the tooth root therewith at less than full scale relative to the crown. Representing the root at about ¾ the full scale of the crown will usually do. Once the crown and root images are aligned, the root image can then be incrementally increased in size until any part of the root touches a corresponding point in the crown. When this contact occurs, typically at the crown-gingiva line, the expansion of the root is fixed at the contact point and the rate of expansion is proportionately scaled down near the contact point. As other points between the expanding root image and crown image come into contact, similar constraints are imposed and the shape of the root deforms as it expands in a way that approaches the shape of the crown of the tooth. When the root has been expanded and the rims of the crown and root fully coincide, the two files are joined to produce a complete watertight and completely sealed 3-D tooth object, having a crown and a root.

PART TWO

Calculating a Set-Up of the Patient's Teeth

Arriving at a definition of the target placement of a patient's teeth is an initial objective is orthodontic treatment that is carried out with the aid of a computer. In this regard, the computer can impose precision on tooth arrangements and appliance design, automate repetitive procedures and provide an interface for interaction with the orthodontist or other human decision makers.

VII. Orientation of Teeth

Figure 35A:
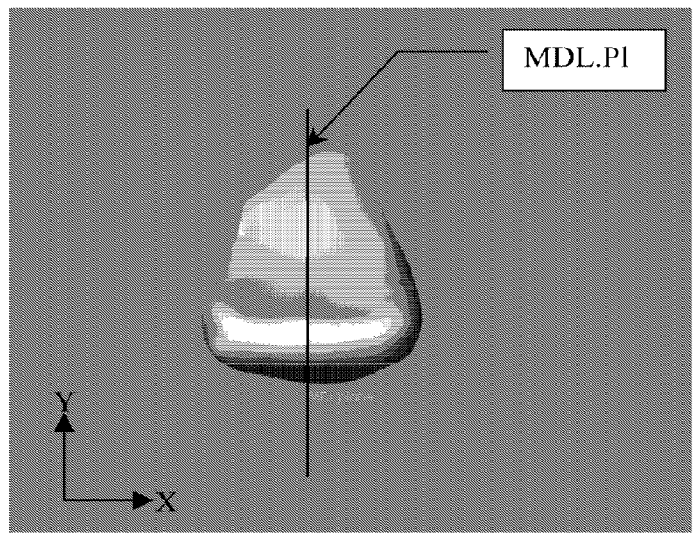
FIGS. 35A-35H are computer screen illustrations showing tooth geometric parameters.
Figure 35B:
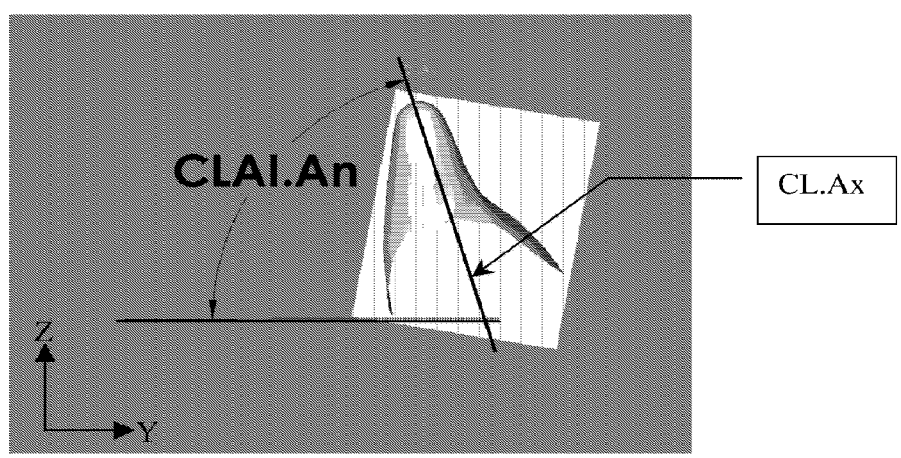

The calculation of tooth finish positions of a custom set-up begins with the assembling of the individual 3-D tooth objects in positions relative to each other. Each of the 3-D tooth objects is oriented relative to an X-Y occlusal plane. For lower teeth and upper incisors, the tooth objects are oriented such that their mid-developmental lobe planes (MDL.Pl) are perpendicular to this X-Y plane, pass through the origin and are parallel to the Y-axes and the Z-axis, as shown in FIG. 35A. For each tooth, the Y-axis is, at this point in the procedure, distinct for each respective tooth and taken as pointing in the lingual direction. The Z-axis for each tooth is the same, taken as pointing in the occlusal direction. The crown long axis (CL.Ax) is initially set at a crown long axis inclination angle (CLAI.An), in the Y-Z plane or MDL.Pl, from a lookup table, Table A, of predetermined torque angle values, as illustrated in FIG. 35B.

TABLE A

TABLE-US-00001

| Tooth Type | Maxillary CLAI.An | Mandibular CLAI.An |
|---|---|---|
| Central | 63 | 73 |
| Lateral | 58 | 73 |
| Cuspid | 72 | 80 |
| 1$^{st}$ Bicuspid | 86 | 97 |
| 2$^{nd}$ Bicuspid | 86 | 100 |
| 1$^{st}$ Molar | 86 | 100 |
| 2$^{nd}$ Molar | 86 | 105 |

Figure 35C:
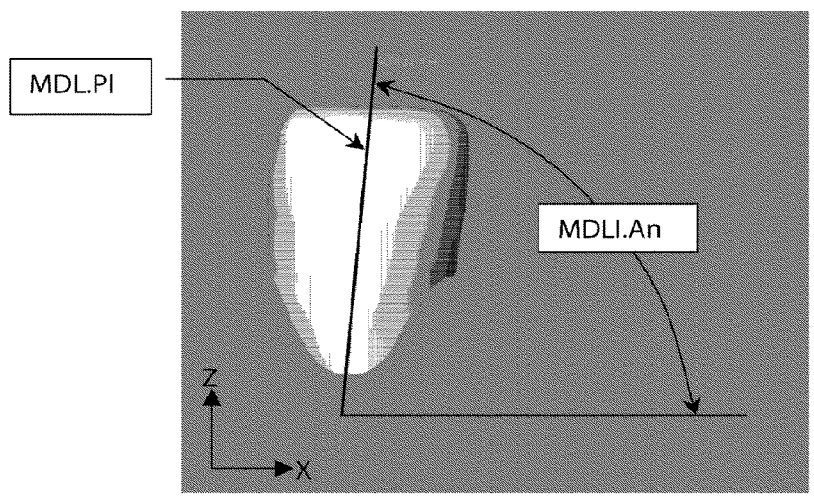

Then, each of the 3-D tooth objects is oriented relative to an X-Y occlusal plane such that its mid-developmental lobe plane (MDL.Pl) is at a predetermined mid-developmental lobe plane inclination or tip angle (MDLI.An), relative to the X-Y plane, from a lookup table, Table B. This angle is shown in the X-Z plane in FIG. 35C. For each tooth, the X-axis for each tooth is distinct at this point in the procedure, and taken as pointing in the distal direction, the Z-axis for each tooth being the same and taken as pointing in the occlusal direction.

TABLE B

TABLE-US-00002

| Tooth Type | Maxillary MDLI.An | Mandibular MDLI.An |
|---|---|---|
| Central | 85 | 88 |
| Lateral | 81 | 86 |
| Cuspid | 80 | 84 |
| 1$^{st}$ Bicuspid | 90 | 87 |
| 2$^{nd}$ Bicuspid | 86 | 87 |
| 1$^{st}$ Molar | 90 | 90 |
| 2$^{nd}$ Molar | 90 | 90 |

Figure 35D:
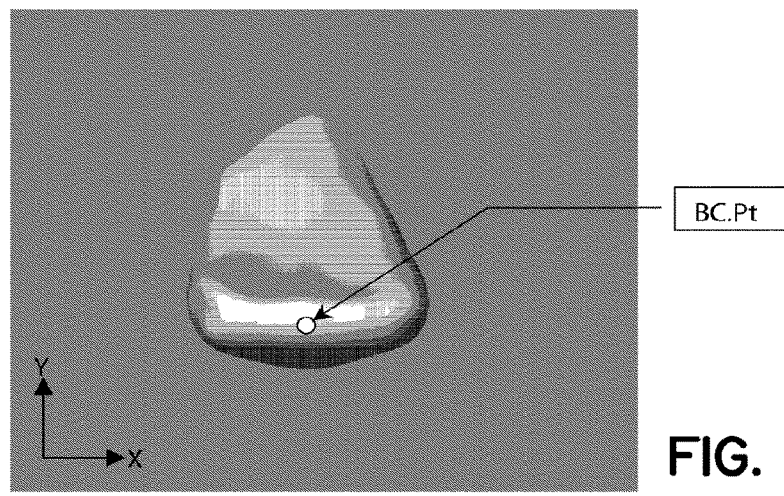
Figure 35E:
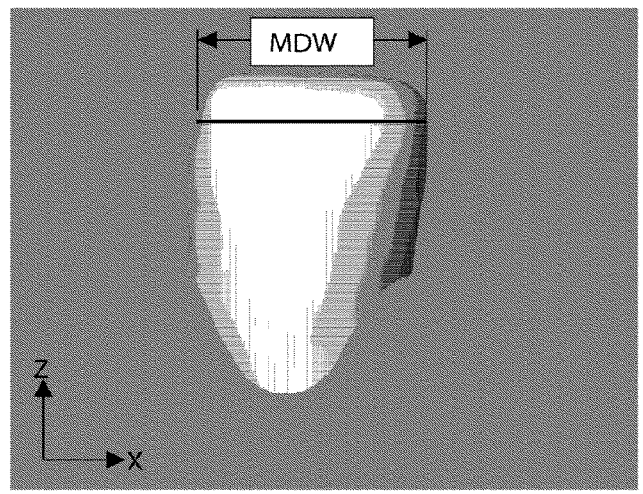

With the tooth in this placement orientation (PO) and viewing the tooth gingivally, in the negative-Z direction and perpendicular to the X-Y plane, the buccal cusp point (BC.Pt) is identified, as illustrated in FIG. 35D. This point (BC.Pt) is used to fit the tooth to, or align it on, a best-fit-buccal-cusp-equation (BCBFE). Then, in an enface view of the tooth with the tooth still in this placement orientation (PO), the greatest width of the tooth is determined at a section of the tooth selected near its incisal edge and parallel to the X-Y plane (FIG. 35E). This width is defined as the mesial-distal width (MDW) of the tooth.

Figure 35F:
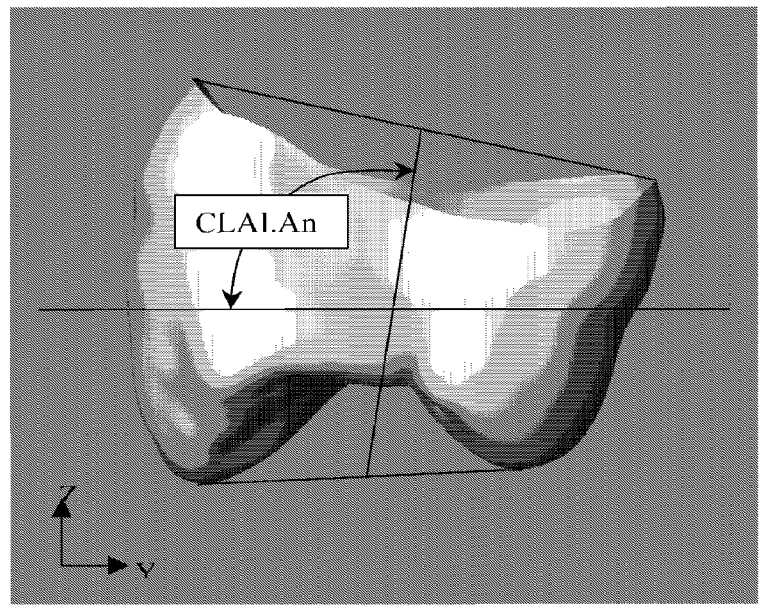
Figure 35G:
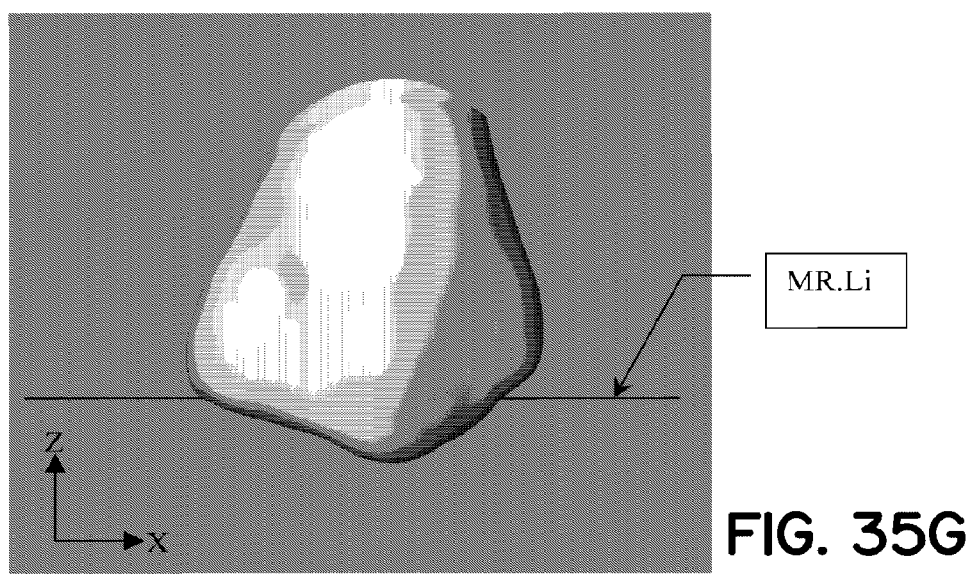
Figure 35H:
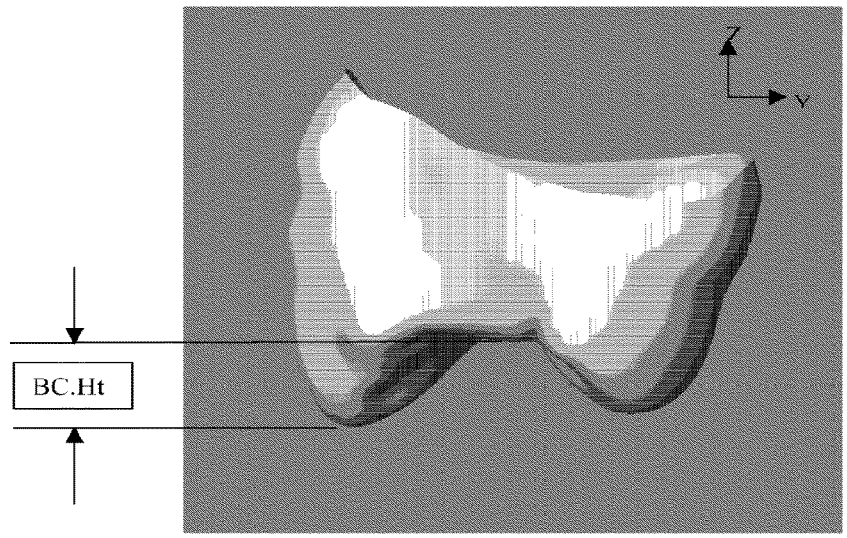

For each of the upper bicuspids and molars, the tooth object is oriented with its CL.Ax at a crown long axis inclination angle (CLAI.An) to the X-Y plane from the lookup table, using the mesial cusps for the molars (FIG. 35F). In the facial view, the tooth object is rotated until MR.Li is parallel to the X-axis (parallel to both the X-Y and X-Z planes), as shown in FIG. 35G. The vertical (Z) distance between the MR.Li and BC.Pt is calculated and recorded as the buccal cusp height (BC.Ht), as illustrated in FIG. 35H.

VIII. Mandibular Tooth Placement

The ideal positions for the mandibular tooth are calculated to initially place the teeth on a mandibular archform equation, for example, the mandibular trough equation referred to as ManTrough (MT). For single cusp teeth (44, 43, 42, 41, 31, 32, 33, 34), beginning at the midline, each of the teeth is positioned at its respective placement orientation (PO) and according to its mesial-distal width (MDW) such that its crown long axis (CL.Ax) intersects ManTrough (MT) and its cervical center-point (CC.Pt) is coincident with ManTrough. The plane mid-developmental lobe plane (MDL.Pl) of the tooth is placed such that the line formed by the intersection of the plane containing ManTrough and MDL.Pl is perpendicular to the curvature of ManTrough. Finally, the arch is made to be symmetrical with respect to the MDWs of the teeth.

For second bicuspids and molars (47, 46, 45, 35, 36, 37), each tooth is positioned at its placement orientation (PO) and according to its mesial-distal widths (MDW) such that the crown long axis (CL.Ax) intersects ManTrough and the cervical center-point (CC.Pt) is coincident with ManTrough. The MDL.Pl of the tooth is positioned such that a line formed by the intersection of the plane containing ManTrough and MDL.Pl is perpendicular to the curvature of ManTrough. The line OT.Li for the tooth is contained within MDL.Pl and is set to be at the occlusal table angle (OT.An) relative to the plane that contains ManTrough. See the Table C below. Finally, the arch is made symmetrical with respect to MDWs.

TABLE C

TABLE-US-00003

| Tooth Type | Maxillary OT.An | Mandibular OT.An |
|---|---|---|
| Central | X | X |
| Lateral | X | X |
| Cuspid | X | X |
| 1$^{st}$ Bicuspid | X | X |
| 2$^{nd}$ Bicuspid | X | 12 |
| 1$^{st}$ Molar | X | 12 |
| 2$^{nd}$ Molar | X | 12 |

Figure 35J:
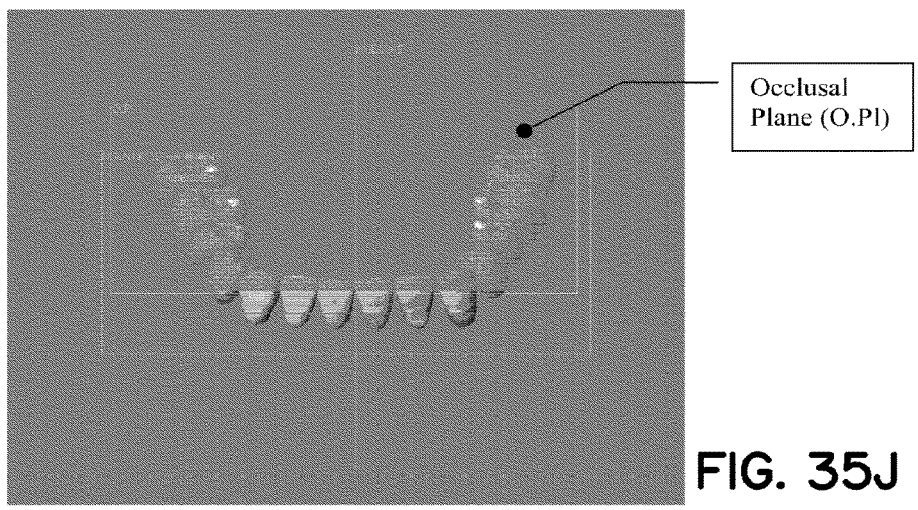
FIGS. 35J-35L are computer screen illustrations showing arrangements of the teeth in relation to an occlusal plane.

The mesial-facial cusp points (MFC.Pt) of both lower first molars and buccal cusp point (BC.Pt) of a lower central, taken as the lower right central, for example, are selected to define the occlusal plane (O.Pl). The constraint that keeps the CC.Pt coincident with ManTrough is then released, and the other teeth are extruded or intruded along their respective CL.Ax's until their BC.Pt's are coincident with this plane (FIG. 35J).

Figure 35K:
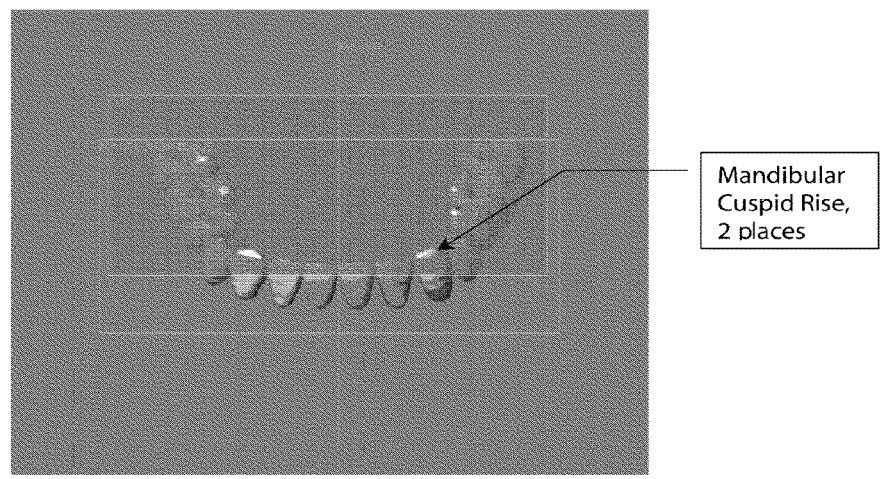

The following equations are used to determine the cuspid rise, that is, the distance that the cuspid cusp tip will project above the occlusal plane. First, the constraint that keeps the cuspid cusp tips coincident with the occlusal plane that contains the buccal cusps of the other teeth is released. The maximum value (in millimeters) is found of the four cuspid rise factor (CRF) equations shown below. The larger value of the BC.Ht of both the left and right teeth in the equations is used. CRF=(1.67.times.BC.Ht of 2.sup.nd Molar)+0.5 CRF=(1.50.times.BC.Ht of 1st Molar)+0.5 CRF=(1.36.times.BC.Ht of 2.sup.nd Bicuspid)+0.5 CRF=(1.20.times.BC.Ht of 1st Bicuspid)+0.5T Then, the cuspid rise is calculated from: Mandibular cuspid rise=34% of the cuspid rise factor Maxillary cuspid rise=66% of the cuspid rise factor The maxillary cuspid rise value is stored for use in the maxillary tooth placement setup. The mandibular cuspid rise is applied by extruding the cuspids in a direction normal to the plane of ManTrough (or the occlusal or X-Y plane) the value determined by the cuspid rise equation, as illustrated in FIG. 35K.

The primary archwire plane (PAW.Pl) is determined by three points taken from the two lower first molars and one lower incisor. In plane MDL.Pl, for both lower first molars, the distance perpendicular to the occlusal plane from BC.Pt to FEGJ.Pt is calculated, then averaged and bisected. This distance becomes the posterior primary archwire height. In the MDL.Pl this posterior primary archwire height is measured gingivally perpendicular to the occlusal plane from BC.Pt and the intersections are found with the tooth facial surfaces at that height. These intersection points become right and left posterior primary archwire points (RPPAW.Pt, LPPAW.Pt).

In plane MDL.Pl for the lower right central (41), the distance perpendicular to the occlusal plane from BC.Pt to FEGJ.Pt is determined. This distance becomes the anterior primary archwire height In this MDL.Pl, this anterior primary archwire height is measured gingivally perpendicular to the occlusal plane from BC.Pt and find the intersection with the tooth facial surface at that height. This intersection point becomes the anterior primary archwire point (APAW.Pt).

Figure 35L:
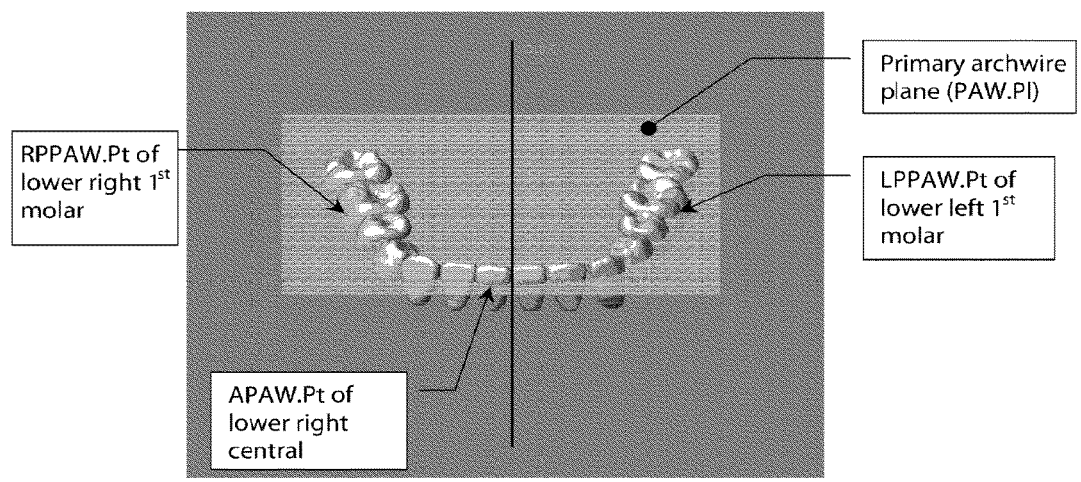

The primary archwire plane (PAW.Pl) is defined through points RPPAW.Pt, LPPAW.Pt, and APAW.Pt. For each tooth, the intersection of the PAW.Pl and the tooth facial surface in the MDL.Pl is defined as the primary archwire point (PAW.Pt). This plane approximates the position of the final archwire plane and is used to filter anatomical variances and promote symmetry. See FIG. 35L.

Figure 35M:
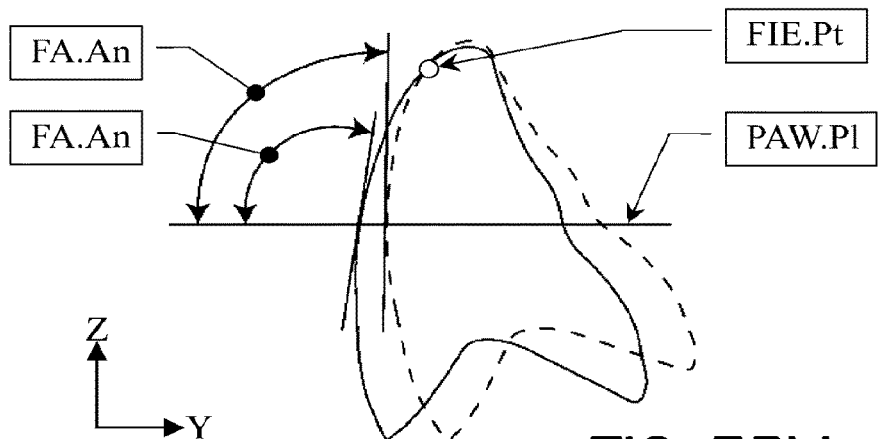
FIGS. 35M-35R are diagrams illustrating alignments of individual teeth in a setup calculation.
Figure 35N:
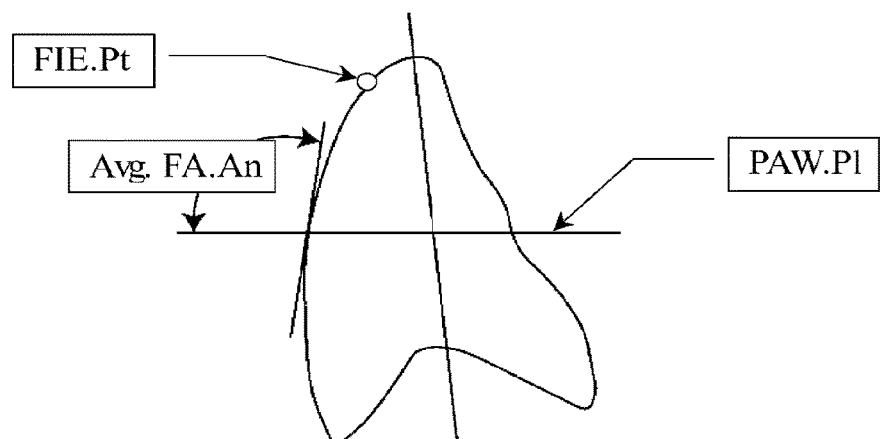
Figure 35O:
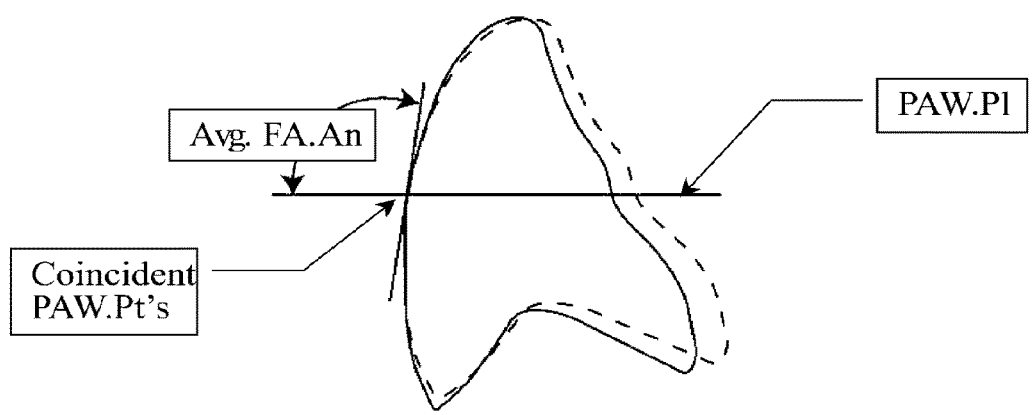

A symmetric arch is then created. The constraint that keep the CL.Ax coincidental to ManTrough for each tooth is released. For each pair of teeth, 41,31 and 42,32, their MDL.Pl cross-sectional views are overlaid and their respective facial incisal edge points (FIE.Pt) are made coincident. The values of both facial axis angles (FA.An) relative to the PAW.Pl are examined and the teeth are rotated about the FIE.Pt until those facial angles are at an average value. This is done at the expense of minor variations in in-out symmetry, as seen in FIGS. 35M & 35N.

Figure 35P:
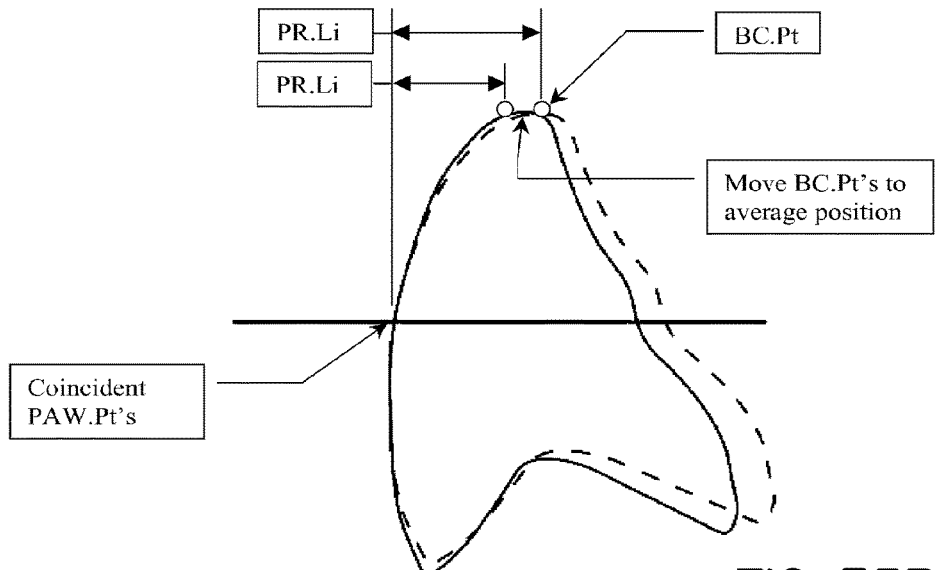
Figure 35Q:
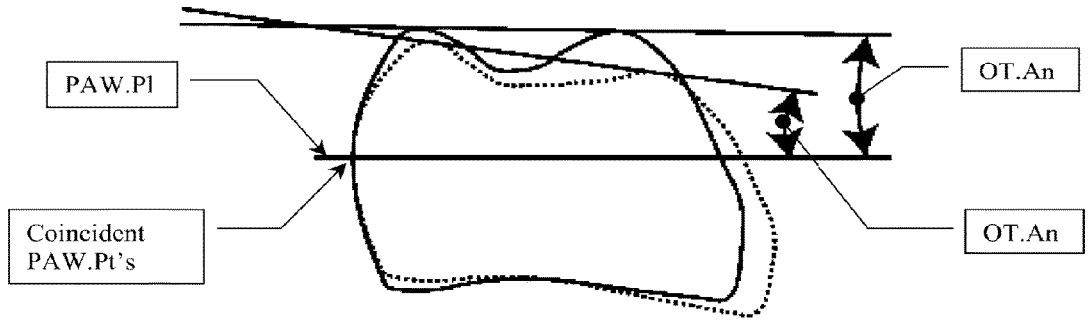
Figure 35R:
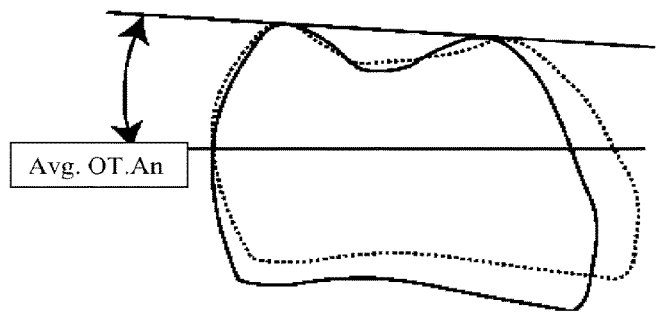

For each pair of teeth, 43,33 and 44,34, their MDL.Pl cross-sectional views are overlaid and both PAW.Pt's are made coincident. The values of both facial axis angles (FA.An) relative to the PAW.Pl are examined and the teeth are rotated about the PAW.Pt until those facial angles are at an average value, as seen in FIGS. 35Q & 35R.

Each of these teeth is then extruded or intruded in a direction normal to occlusal plane (O.Pl) until its BC.Pt is again coincident with the occlusal plane. The horizontal distance from the buccal cusp point (BC.Pt) to PAW.Pt is defined as the prominence line (PR.Li), which is re-established to an average value by adjusting BC.Pt of the teeth (FIG. 35P).

For each pair of teeth, 47, 37, 46, 36 and 45, 35 their MDL.Pl cross-sectional views are overlaid and both PAW.Pts are made coincident. The values of both occlusal table angles (OT.An) are examined relative to the PAW.Pl and the teeth are rotated about the PAW.Pt until those occlusal table angles are at an average value. (FIGS. 35Q & 35R.)

The teeth are extruded or intruded in a direction normal to occlusal plane (O.Pl) until the BC.Pts are again coincident with the occlusal plane. The horizontal distance from the buccal cusp point (BC.Pt) to PAW.Pt is defined as the prominence line (PR.Li), which is reestablished to an average value by adjusting the BC.Pts. (FIG. 35P.)

Figure 35S:
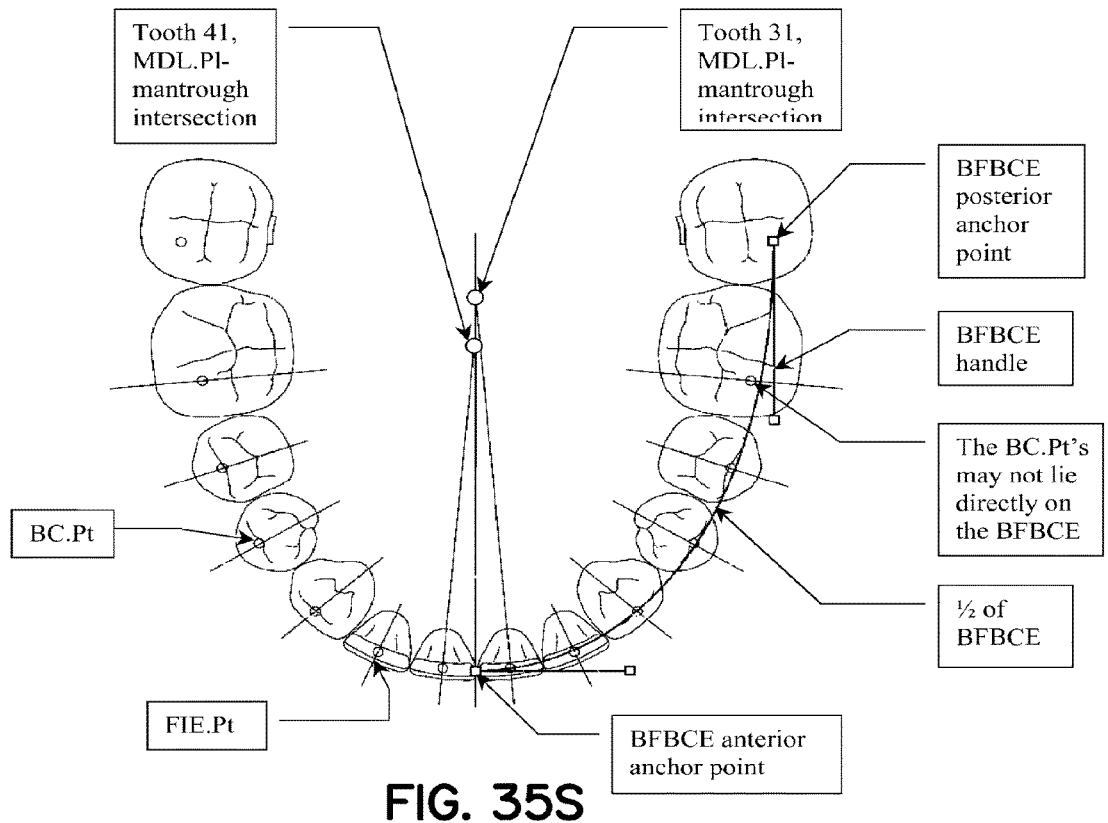
FIGS. 35S-35X are diagrams illustrating relative positioning and orientations of teeth in a setup determination.

The FIE.Pts of teeth 42, 41, 31, 32 are fixed to align the lower incisal edges to BFBCE to enable placement of upper incisors. The BC.Pt of teeth 42, 41, 31, 32 are reset to an average value from FIE.Pt along MDL.Pl. The intersection of MDL.Pl and midline from mantrough grid for 41, 31 is found and the line segment distance from BC.Pt along MDL.Pl to intersection for both teeth is calculated. From the intersections, the respective distance equal to line segment is measured facially along midline. Points are created at measured distance on midline and averaged. This averaged point becomes the origin of the anterior bezier handle and the mesial facial cusps of 47, 37 become the posterior bezier handles. An operator can move the handles to adjust the curve, which becomes the default best fit buccal cusp equation (BFBCE). (FIG. 35S.)

Figure 35T:
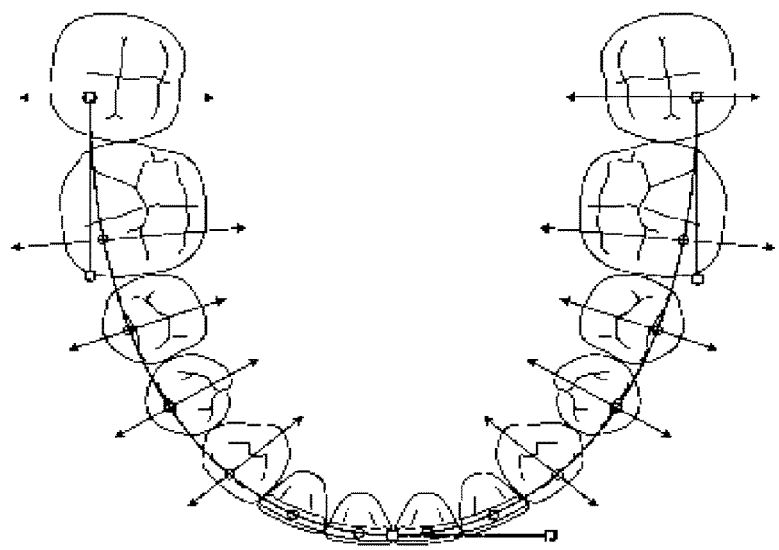

Each tooth, other than 42, 41, 31, 32, is moved either facially or lingually normal to the buccal cusp equation such that the individual cusp tips (BC.Pt)s fall on that curve. (FIG. 35T.)

Modifications are then made by the operator to the Computer Setup. The operator has the ability to make small translational modifications in MDL.Pl, rotational modifications about the CL.Ax, and rotational modifications about the PAW.Pt when viewed facially (in the X-Z plane), for each tooth. After each and every individual modification the mandibular arch setup is recalculated to obey the rules described above while accommodating each specific change.

Additional modifications include BFBCE adjustments. The operator has the ability to pull on the bezier handles to dynamically effect one of two different results: (1) Default-Translational movements of each tooth may be made in their respective MDL.Pls with the BC.Pts coincident with the BFBCE; and (2) Torque (or facial axis angle) adjustments may be made because the BC.Pts are coincident with the BFBCE and each tooth is rotated about its respective cervical center point (CC.Pt) in its respective MDL.Pl.

IX. Maxillary Tooth Placement

Figure 35U:
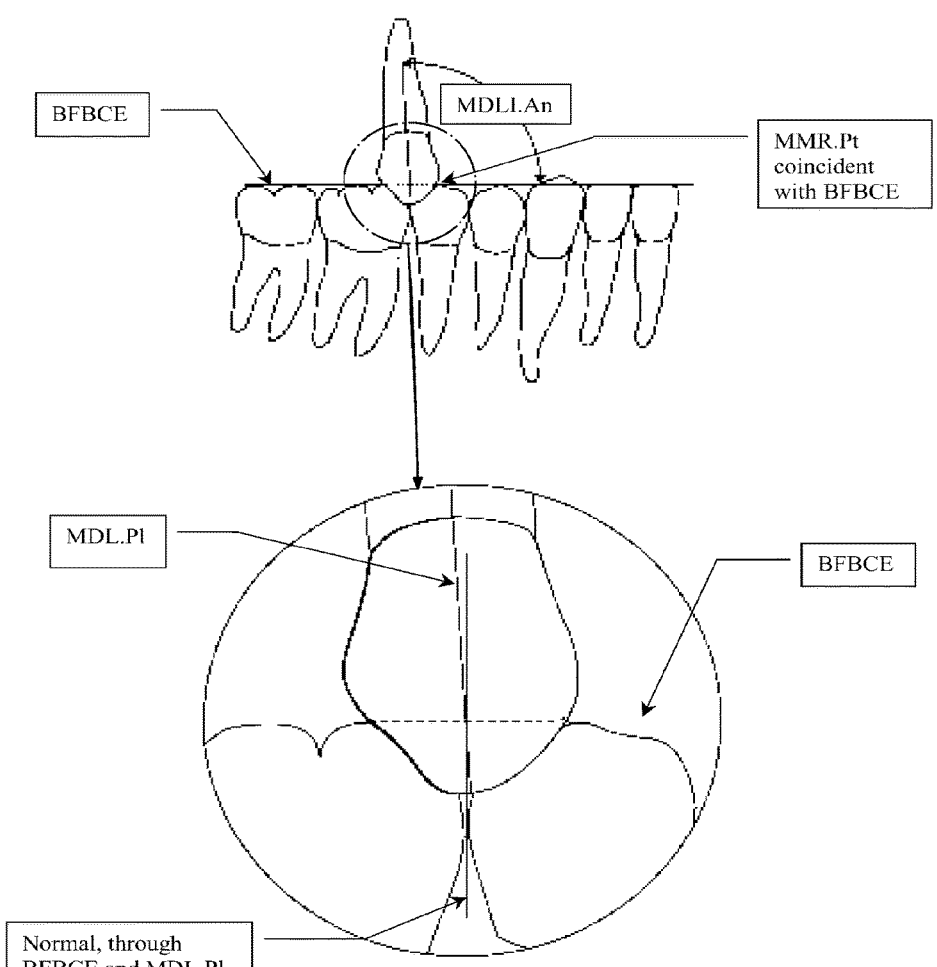

First the bicuspids (15, 14, 24, 25) are placed. At their placement orientation (PO), the bicuspids are placed such that their respective mesial marginal ridge points (M.Pt) are coincident with BFBCE at angle MDLI.An as found in the lookup table. A line of intersection of MDL.Pl and the plane of BFBCE will be perpendicular to BFBCE. A normal from the intersection of the MDL.Pl and BFBCE will be coincident with the mandibular 2.sup.nd bicuspid/1.sup.st molar embrasure (for maxillary 2.sup.nd bicuspids) or the mandibular 1.sup.st bicuspid/2.sup.nd bicuspid embrasure (for maxillary 1.sup.st bicuspids). See FIG. 35U.

Molars (17, 16, 26, 27) are placed at their Placement Orientation (PO) such that their respective MMR.Pts are coincident with BFBCE, are in contact with the maxillary 2.sup.nd bicuspids for 1.sup.st molars or with the maxillary 1.sup.st molars for 2.sup.nd molars, the respective MDLI.An are as found in the lookup table, and their Stolar.Li of occluding pairs are parallel when viewed perpendicular to the X-Y plane.

Figure 35V:
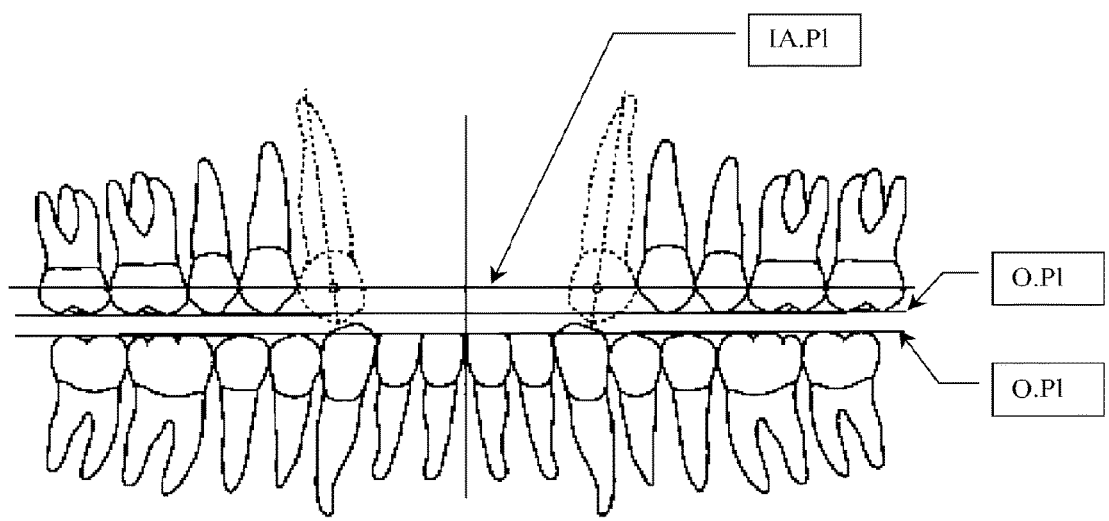

Incisors (12, 11, 21, 22), the previously stored values of maxillary cuspid rise are used, cuspid MDLI.An, and cuspid MDW to simulate maxillary cuspid placement. (FIG. 35V.) In the figure, the upper and lower teeth are separated for clarity and the occlusal plane is shown twice. The incisor alignment plane (IA.Pl) is created through the FA.Pts of the cuspids and parallel to occlusal plane (O.Pl).

Figure 35W:
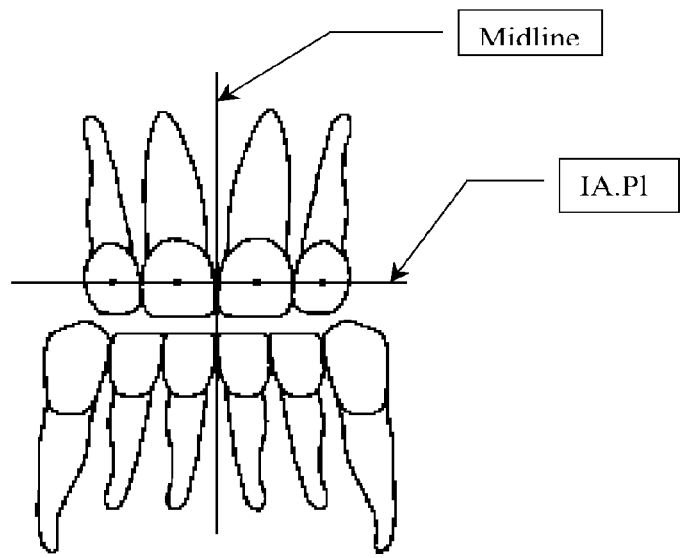

At their Placement Orientation (PO), the centrals and laterals are placed such that their FA.Pts are coincident with the IA.Pl, their mesial extremities are coincident with the midline for centrals or coincident with the centrals for laterals, and the teeth are in contact with the mandibular incisors. (FIG. 35W.) In this figure also, the upper and lower teeth are separated for clarity.

Figure 35X:
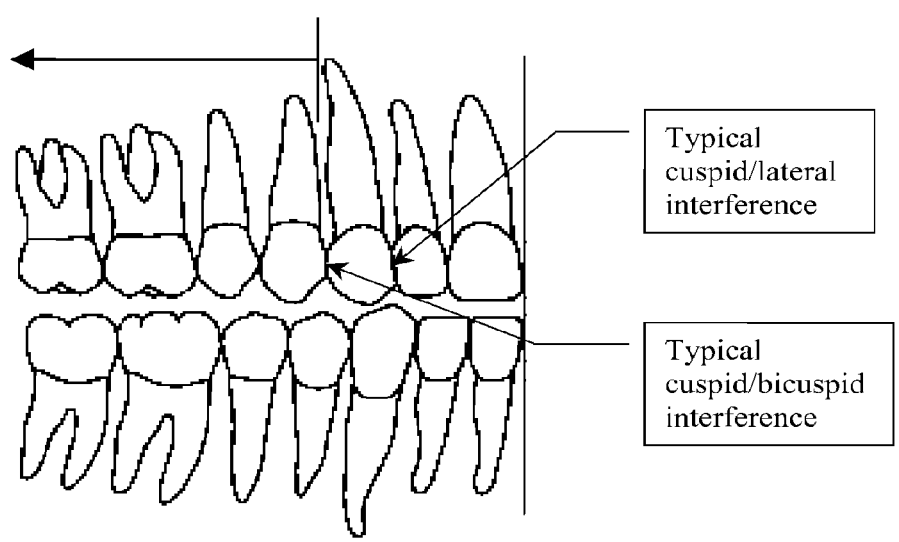

Cuspids (13, 23) are placed at their Placement Orientation (PO) such that their FA.Pts are coincident with the IA.Pl, they fit mesial-distally between the maxillary laterals and 1.sup.st bicuspids, and they are in contact with the mandibular cuspids and 1.sup.st bicuspids. This placement generally results in an interference with the adjacent teeth. This interference will be allowed in the setup and will be resolved physiologically in time. (FIG. 35X.)

Minor Modifications to the Computer Setup are then made by the operator. The operator has the ability to make small translational modifications in MDL.Pl, rotational modifications about the CL.Ax, and rotational modifications about the FA.Pt or PAW.Pt, depending on the tooth, when viewed facially (X-Z plane), for each tooth in the maxillary arch. After each and every individual modification the maxillary arch setup is recalculated to obey the rules described above while accommodating each specific change.

X. Extraction Cases

The set-ups for cases that include extractions are also calculated, for various options, as follows:

Mandibular Extraction Only

Figure 35Y:
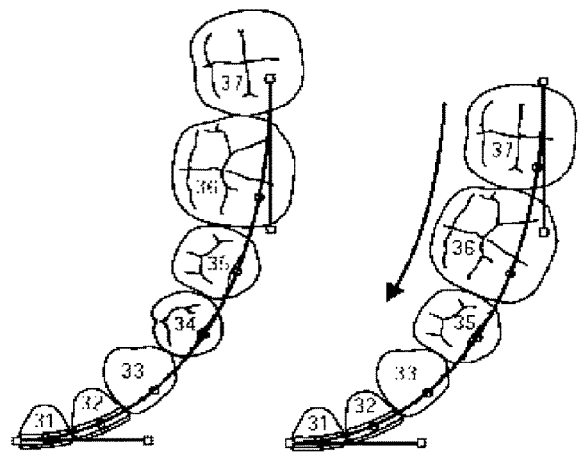
Figure 35Z:
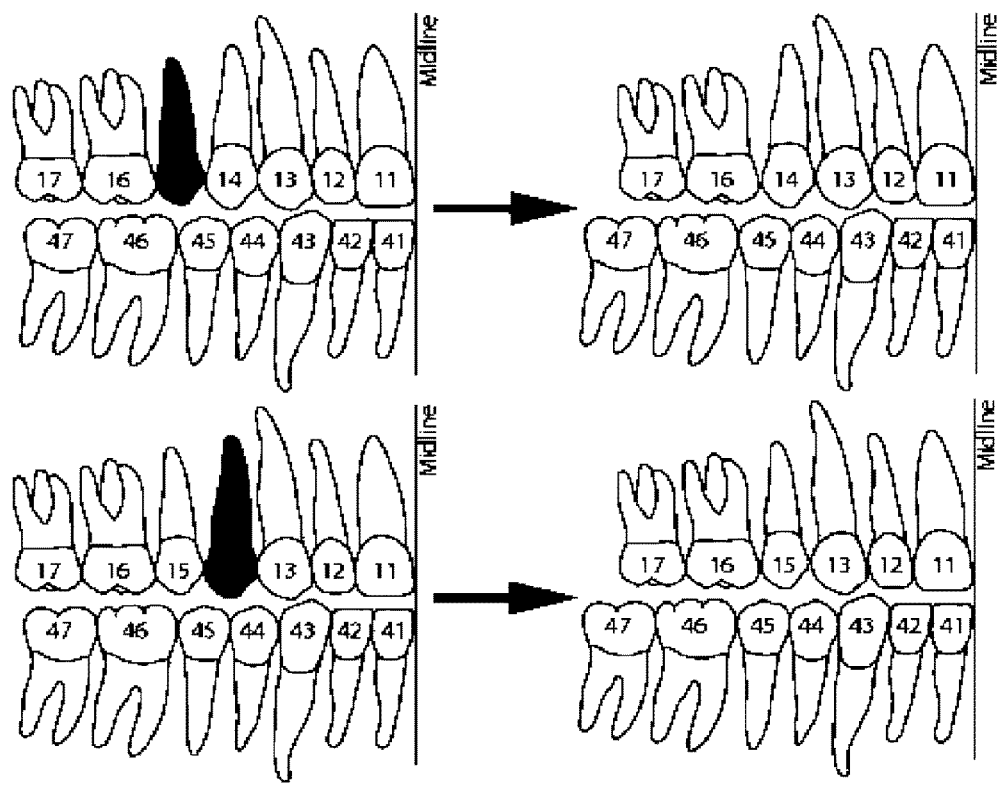
Figure 35A:
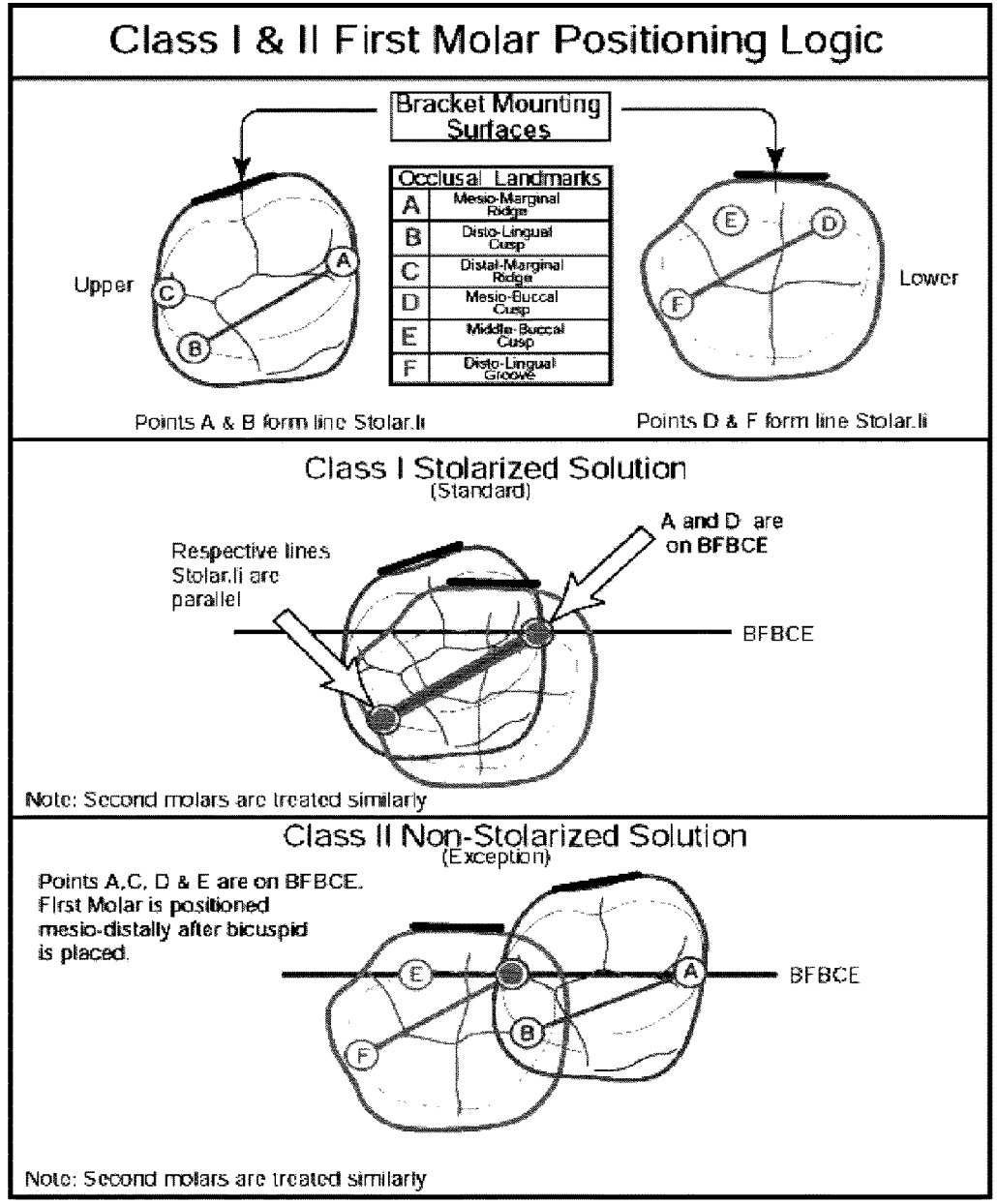
Figure 35B:
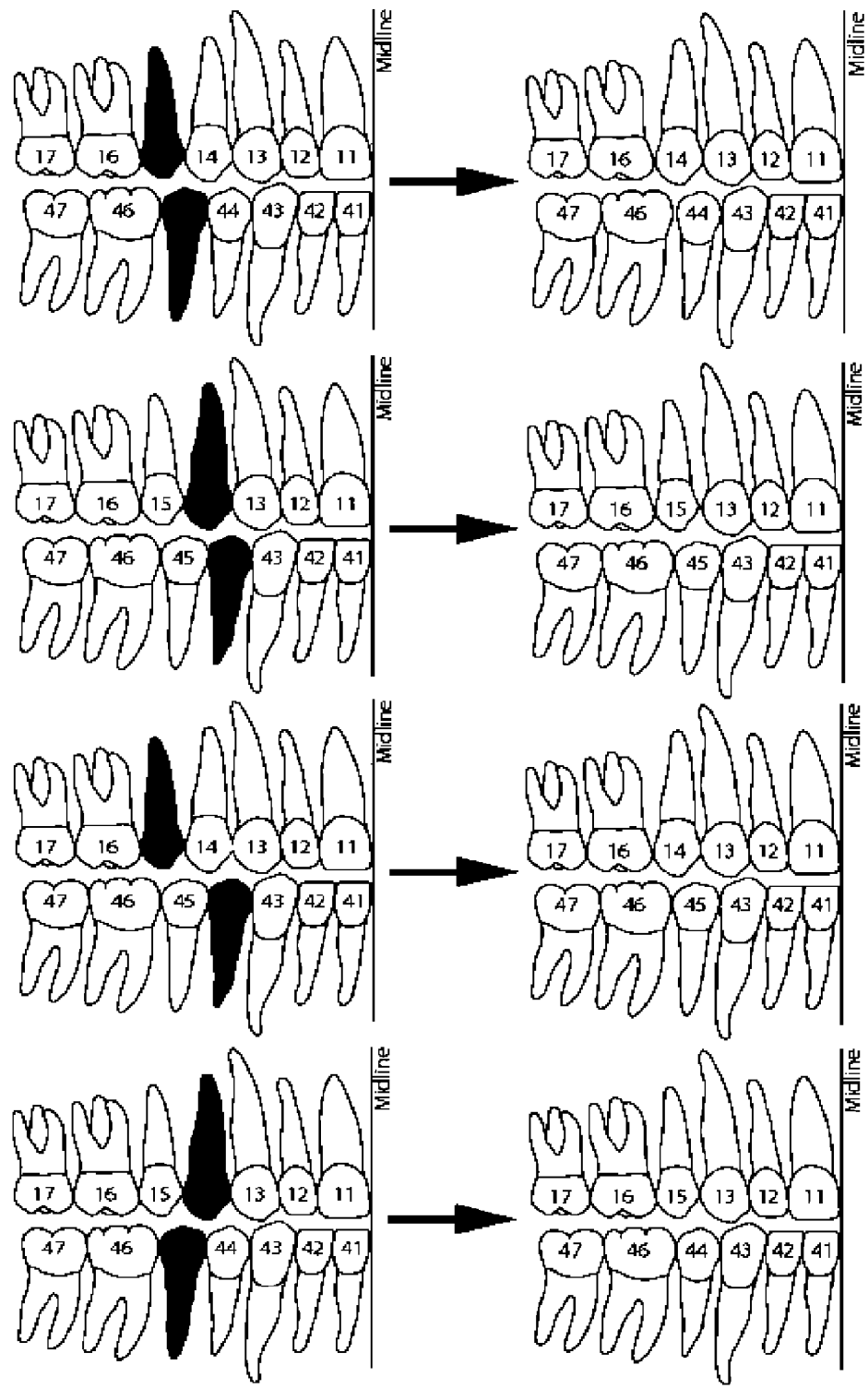
Figure 35C:
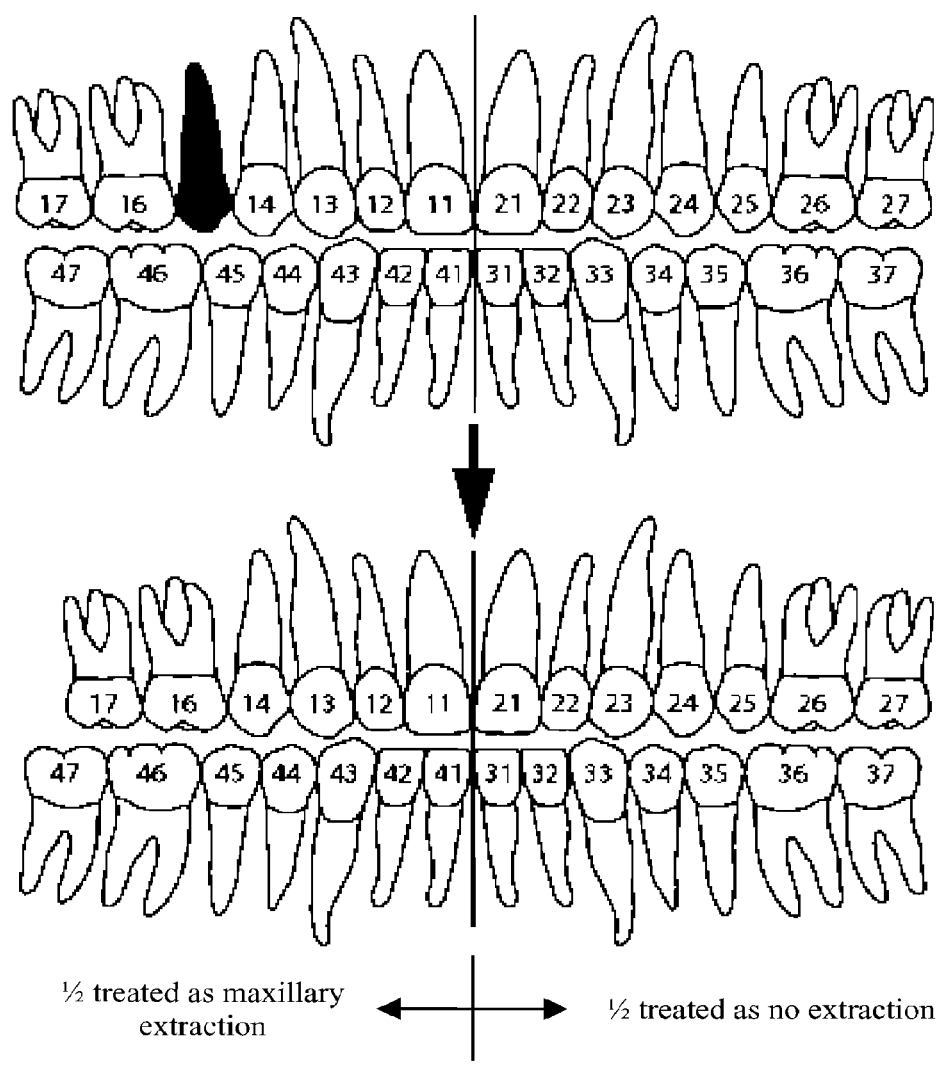
Figure 35D:
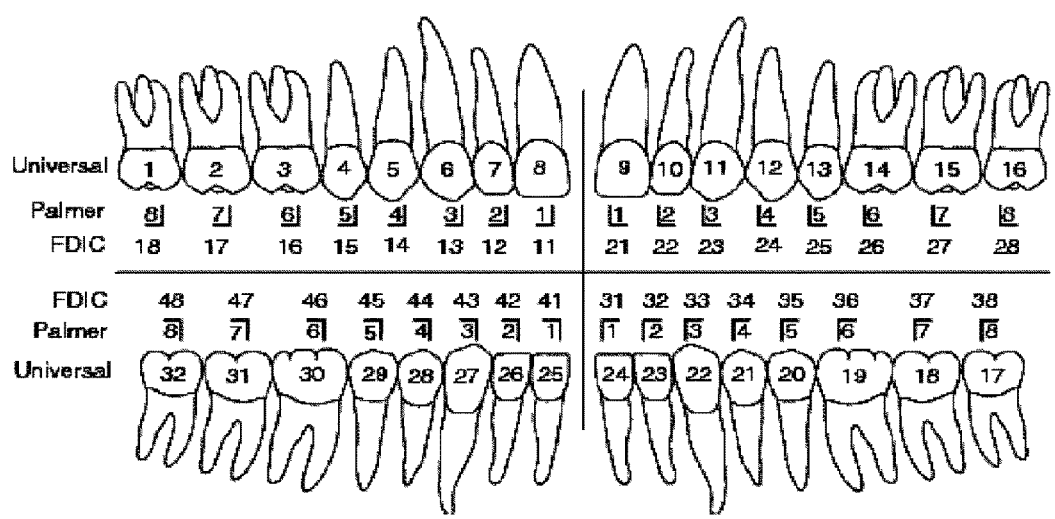

Generally, mandibular extraction cases involve teeth 34, 35, 44 or 45. The different extraction scenarios are as follows: two contralateral teeth may be extracted, teeth 34 and 45 may be extracted, or teeth 35 and 44 may be extracted. The remaining mandibular teeth are placed properly in the setup as described above. The extracted teeth are merely deleted from the placement protocol for non-extraction cases described in VIII-Mandibular Tooth Placement above. The remaining teeth are placed according to their MDW, CL.Ax, CC.Pt, and MDL.Pl also as described in that Phase. See FIG. 35Y. For subsequent steps such as creating a symmetric arch or averaging, again, those teeth are simply deleted from the instruction set and the set-up calculation is then continued.

Maxillary Extraction Only

For maxillary extractions involving two bicuspid extraction, one from each side of upper arch, the lower teeth are arranged as described in Phase VIII-Mandibular Tooth Placement section above. On the maxilla, the remaining bicuspids are the first to be placed. It is placed in the same manner as described in Phase IX, however, the embrasure of the lower teeth that it fits into is shifted based on the teeth that have been removed. FIG. Z shows bow the teeth fit together when this type of extraction case is considered. The molars are placed according to the rules ill FIG. 35AA. Then, the incisors and cuspids are just as in Phase IX.

For mandibular and maxillary extraction involving four bicuspid extractions, two upper and two lower, the lower teeth are arranged as described in the mandibular extraction section above. On the maxilla, the remaining bicuspid is the first to be placed. It is placed in the same manner as described in Phase IX, however, the embrasure of the lower teeth that it fits into is shifted based on the teeth that have been removed. The molars, incisors, and cuspids are then placed just as in Phase IX. FIG. 35BB shows how the teeth fit together when upper and lower bicuspid extraction cases are considered.

General Exception—Asymmetry

There will be times when the number of extracted teeth causes asymmetry in the mouth. When this happens, each half of the mouth is treated independently and is set up according to its respective extraction scenario. See FIG. 35CC.

Alternative tooth identification schemes are illustrated in FIG. 35DD.

PART THREE

Determining the Design of an Orthodontic Appliance

Providing an orthodontic appliance to carry out a determined treatment plan involves using the three-dimensional model of the teeth in their target positions to define geometry of the appliance that fits precisely on the teeth and functions to accurately move the teeth to their target positions. Such a process provides machine code and other instructions that facilitate accurate manufacture of an orthodontic appliance.

X. Appliance Design

After the teeth are setup into a good occlusion, an appliance is designed to position the teeth in the target positions defined in the set-up. Three dimensional surfaces of the teeth may define corresponding surfaces of the appliance that contact the teeth, for example, the bases of brackets, the registration surfaces of placement jigs, etc. These surfaces of the various teeth are connected by the appliance, which is, in the illustrated example, a bracket and archwire brace. These brackets and wires, or other appliances or appliance components, are designed for placement on the teeth.

Figure 36:
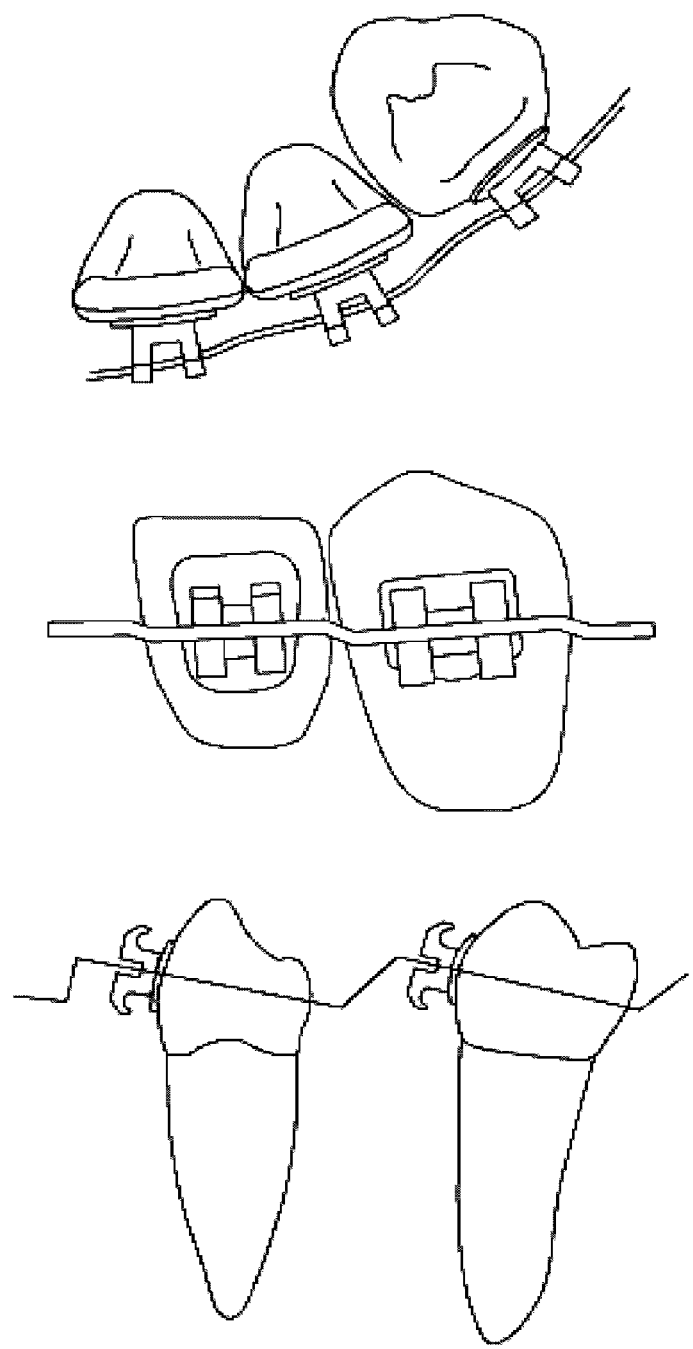
FIG. 36 is a diagram illustrating one acceptable criterium for configuring an archwire.

An archwire is designed to satisfy the following conditions: 1) The wire is symmetrical about the midline. 2) The wire lies, initially, in the archwire plane (PAW.Pl). 3) The wire is perpendicular to each tooth's mid-developmental lobe plane (MDL.Pl). 3) The wire passes through the body of each bracket. Its exact location in the body of the bracket is described in more detail in the Bracket Slot Cutting section below. The location in the bracket should not be at any of the extremes of the charts. 4) The wire curve should be aesthetic, meaning generally U-shaped. 5) The wire extends approximately 2 nm beyond the most posterior of the appliances, which are typically buccal tubes on molars. 6) The wire has a minimum number and magnitude of inflections, or slight bends, and the bends should be confined to and remain in the PAW.Pl (referred to herein as 1.sup.st order bends; bends defined below as 2.sup.nd or 3.sup.rd order bends should be avoided or disallowed, see FIG. 36).

Figure 37A:
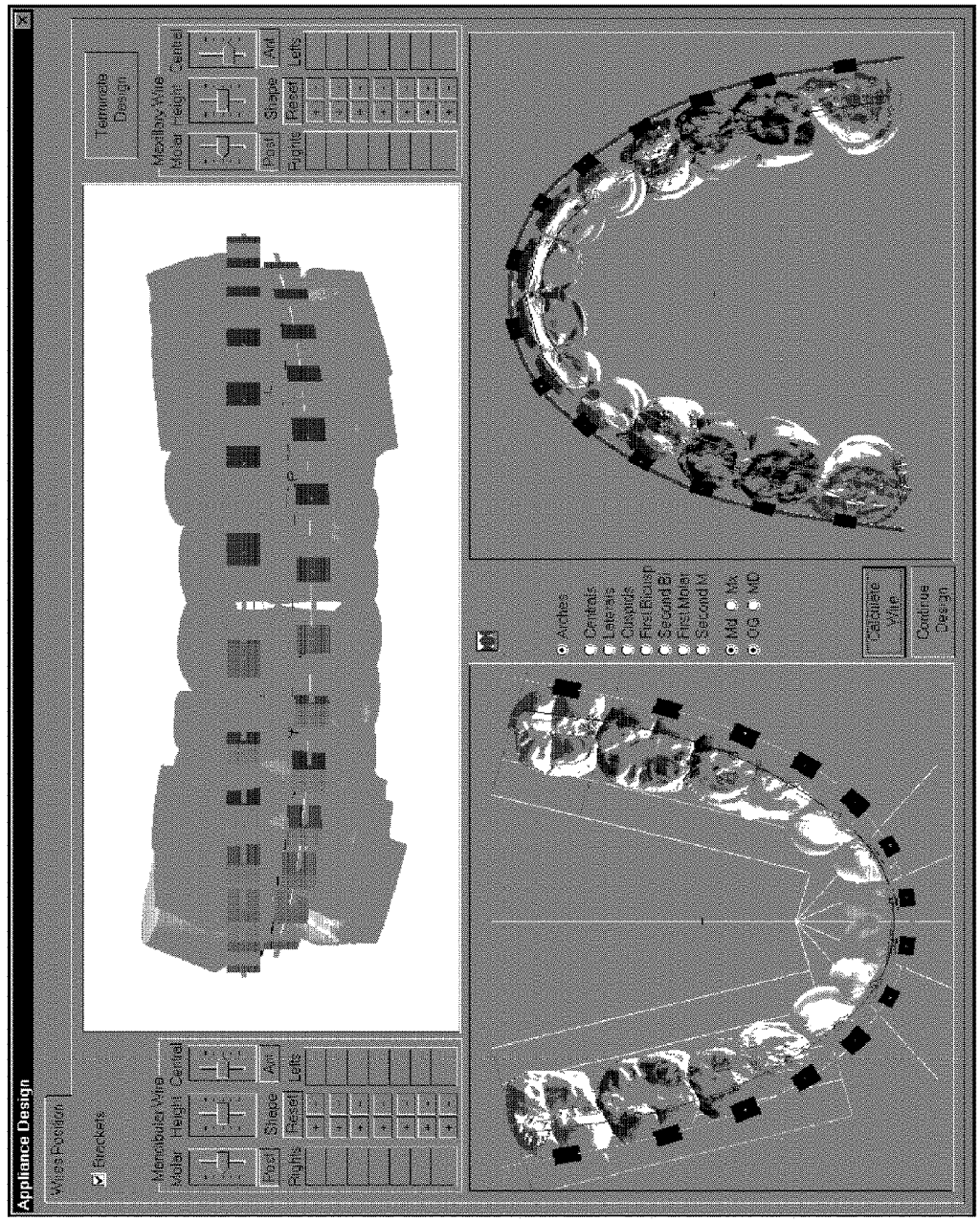
FIG. 37A is a computer screen illustration of a wire design interface.
Figure 37C:
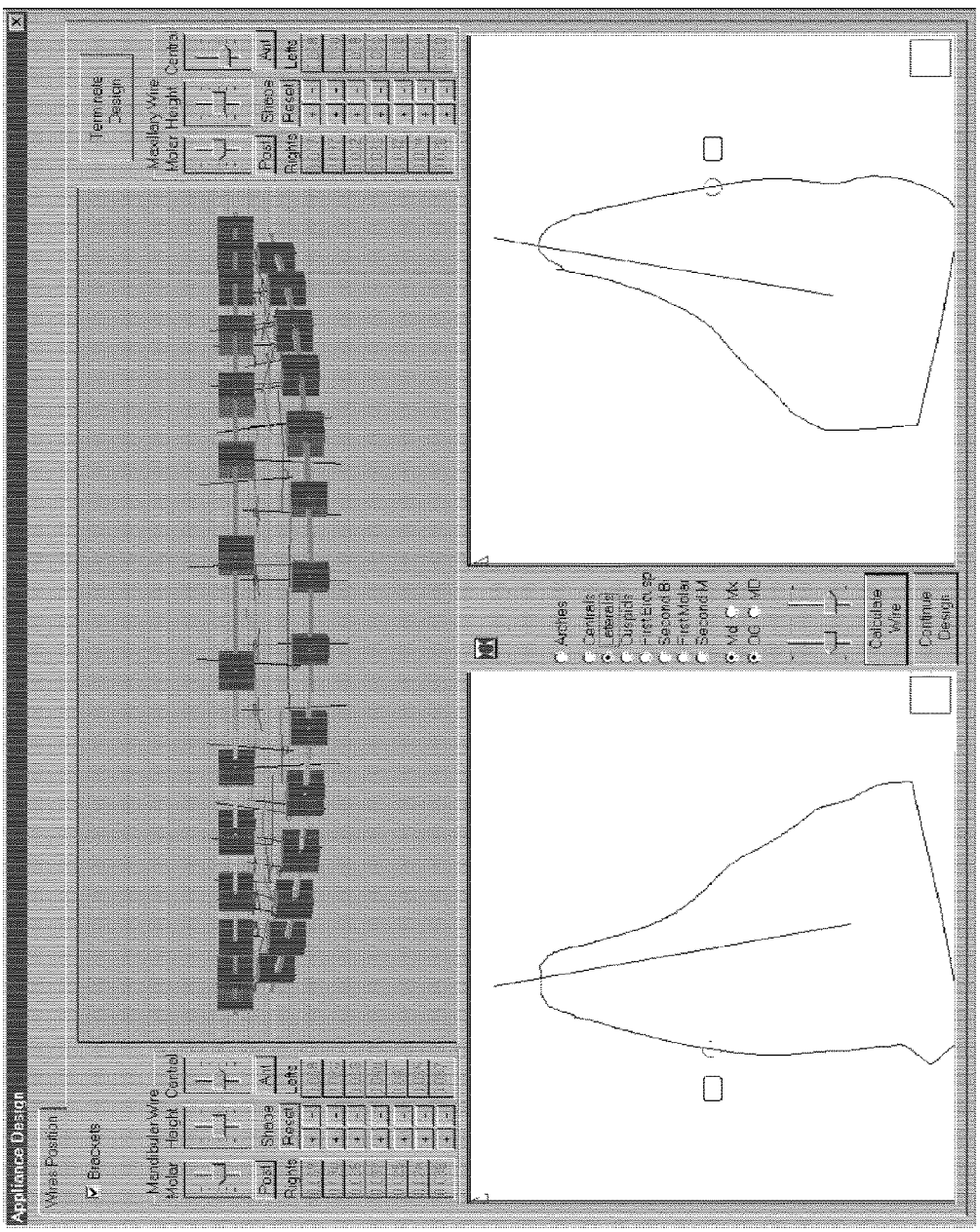
FIG. 37C shows an annotated screenshot illustrating tooth sections relative to the position of an archwire.
Figure 37B:
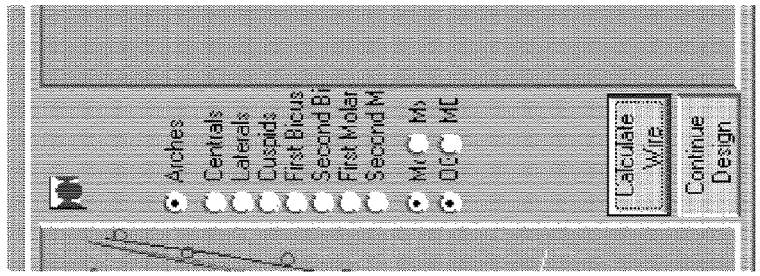
FIG. 37B shows a portion of a screen depicting the selection of different available views.

FIG. 37A shows an annotated screenshot of a wire design interface. The functionality of different views is made available through radio buttons as illustrated in FIG. 37B, through a common display dialog box of the type available for most applications. Sections of the teeth illustrating the position of the archwire are also provided, as illustrated in FIG. 37C.

Figure 38A:
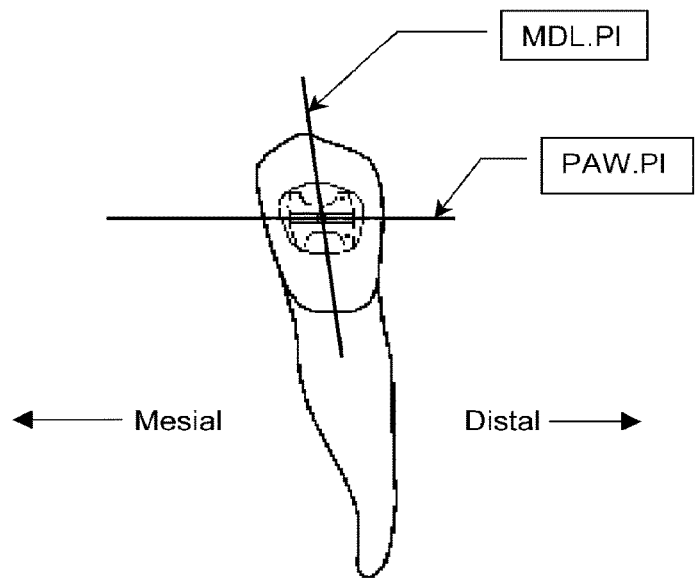
FIG. 38A is a diagram illustrating one acceptable manner of bracket positioning.

The mid-developmental lobe plane (MDL.Pl) defines the initial mesial-distal positioning of the appliance and the primary archwire plane (PAW.Pl) defines the vertical position, as illustrated in FIG. 38A.

XI. Modifications

Figure 38B:
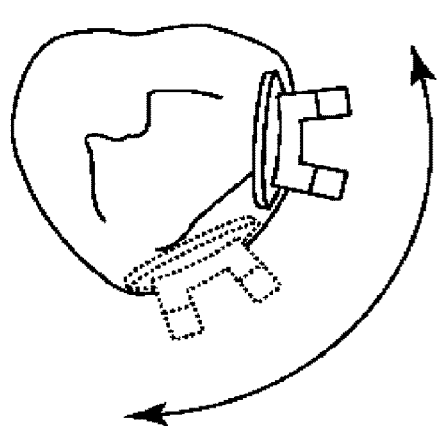
FIGS. 38B and 38C are diagrams illustrating bracket freedoms that may be provided to an operator.
Figure 38C:
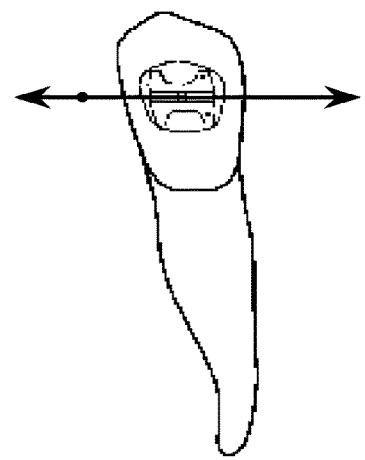

The operator is able to override and adjust the computer's position of the appliances. This operator is typically a skilled person at an appliance manufacturing facility, but can also be a treating orthodontic practitioner. After each and every adjustment, the appliance setup is recalculated to accommodate each specific change, so that the immediate results of each change are immediately apparent to the user or practitioner. FIGS. 38B and 38C shows the bracket freedoms that the operator provided to the operator.

Figure 39:
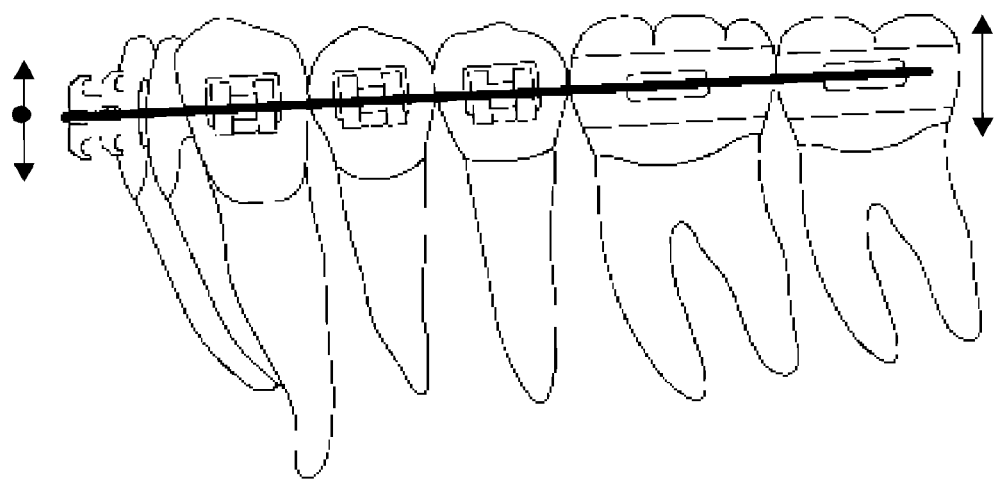
FIGS. 39-40 are diagrams illustrating interactive modification of appliance designs.
Figure 40:
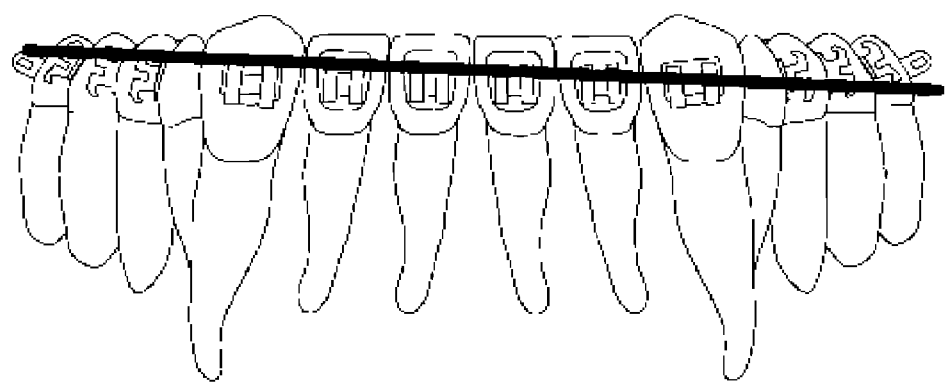

For the archwire, from phase VIII, the plane PAW.Pl is described by the left, right, and anterior primary archwire points (LPPAW.Pt, RPPAW.Pt, APAW.Pt). One or more of those constraints may be released, which gives the archwire the freedoms described in FIG. 39. Also, for the archwire to be oriented as shown in that figure, the brackets are allowed to move along their respective MDL.Pl's to accommodate the new archwire position. Side to side tipping of the archwire plane, as illustrated in FIG. 40, is preferably not allowed.

XII. Bracket Slot Cutting

Bracket manufacture involves cutting or otherwise forming archwire slots into the brackets. Each bracket has a unique slot whose geometry is determined by the location of the archwire in the appliance setup. Just as there were rules with the arch setup, there are rules for designing the bracket slot. The slot should not be so shallow that the archwire protrudes out from the bracket, nor should it be so deep that it interferes with the tooth. Additionally, the angle to which the slot is cut should be limited so as not to cut the tie-wings off or make them weak. Finally, the "slot box" should be centered in the body of the bracket. (FIG. 41). The preferred maximum and minimum slot depths and torques are illustrated in FIG. 42 and FIG. 43.

Figures 43A, 43B:
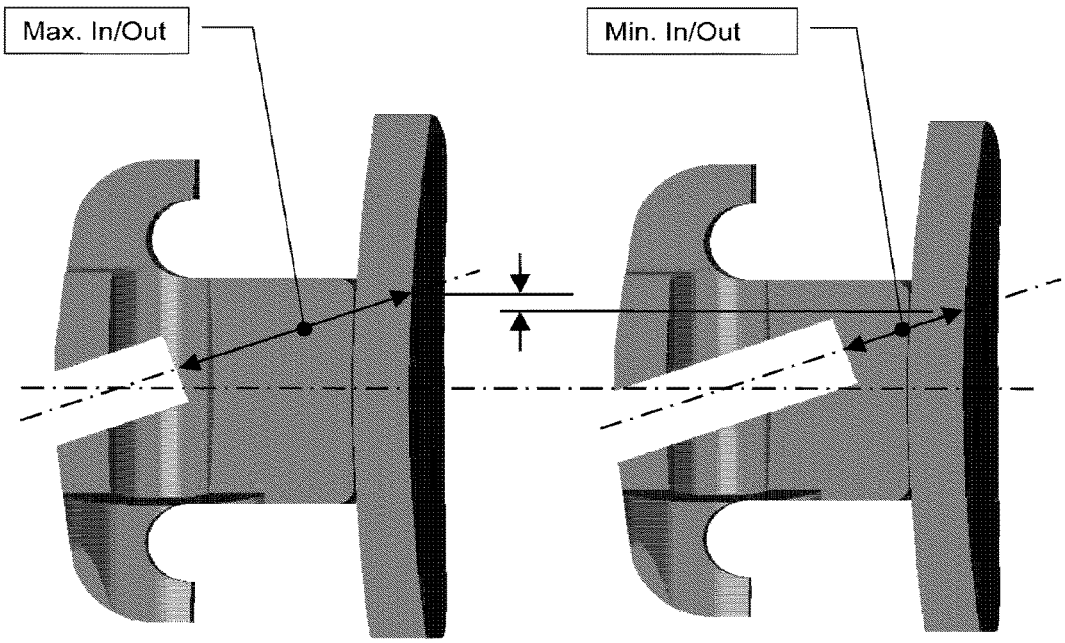
FIGS. 43A-43B, 44, 45, 46A-46C are diagrams illustrating the formation of slots in buccal tubes.

In FIG. 43, the slot depth changes and torque remains constant, the location of the In/Out dimension on the bracket pad changes also (.DELTA.). In order to avoid a weak or fragile bracket, the combination of slot depth and angle (torque) are kept within limits. The charts shown in FIGS. 47-55 describe acceptable values for In/Out Dimensions when compared with Torque. Any value on the chart that falls between the two curves shown is an acceptable value.

Figure 44:
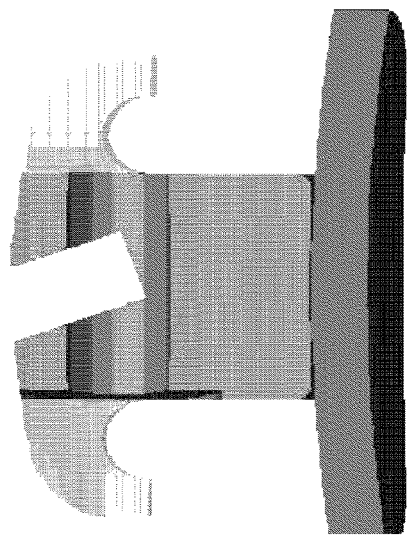
Figure 46A:
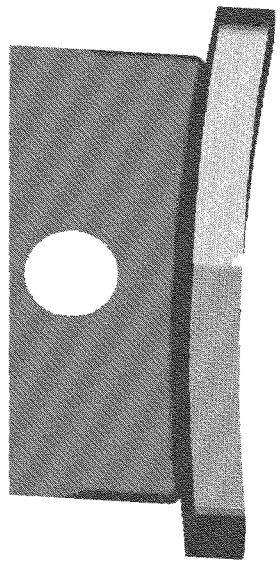
Figure 45:
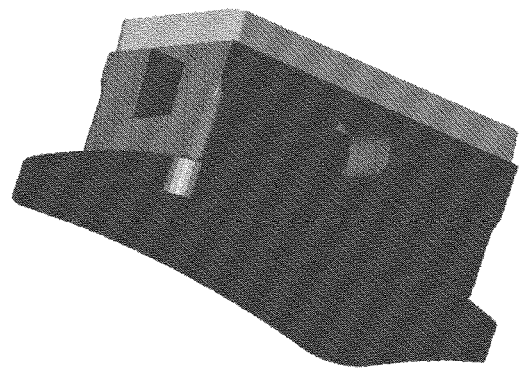
Figure 46B:
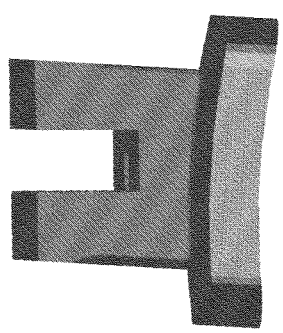
Figure 46C:
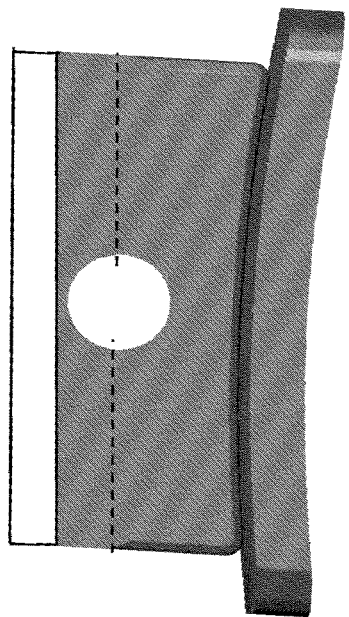
Figure 47:
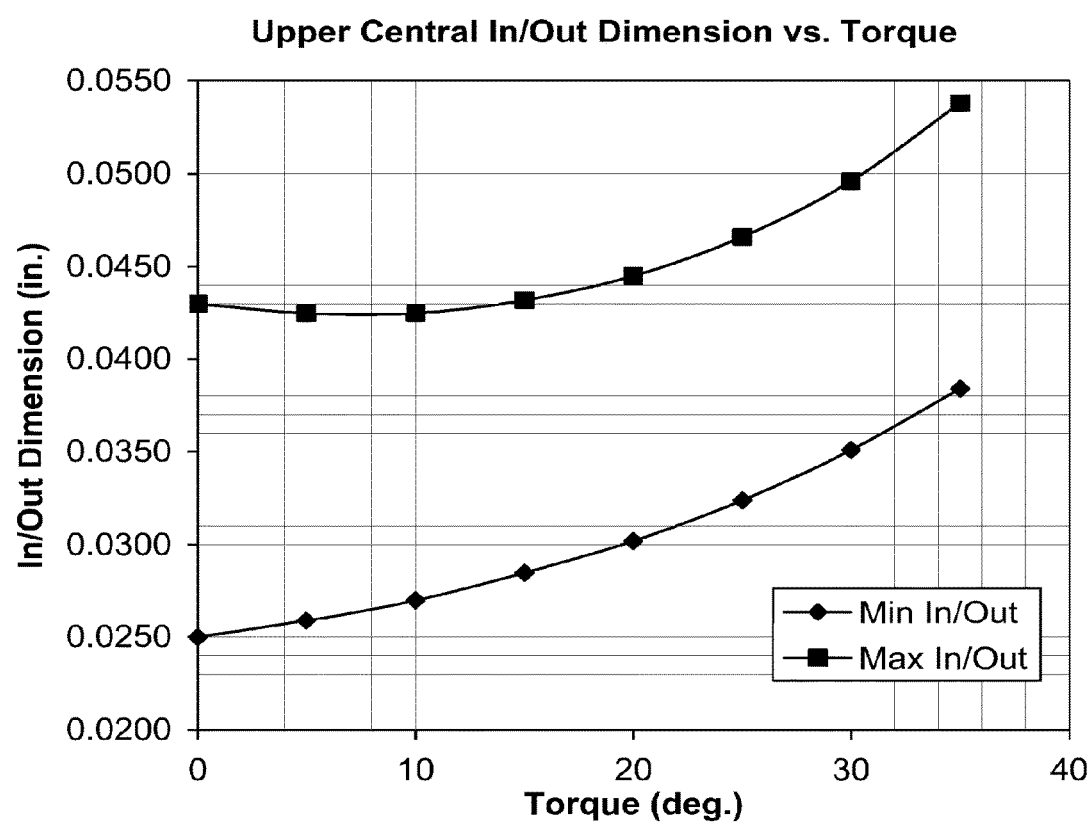
FIGS. 47-55 describe certain acceptable values for in/out dimensions and torque.
Figure 48:
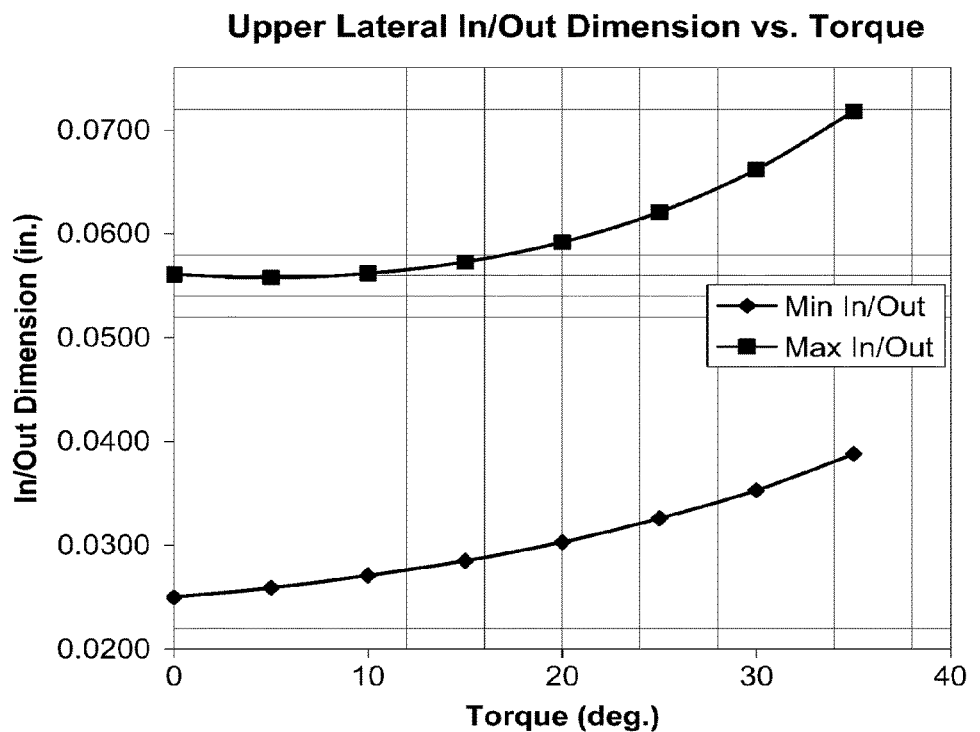
Figure 49:
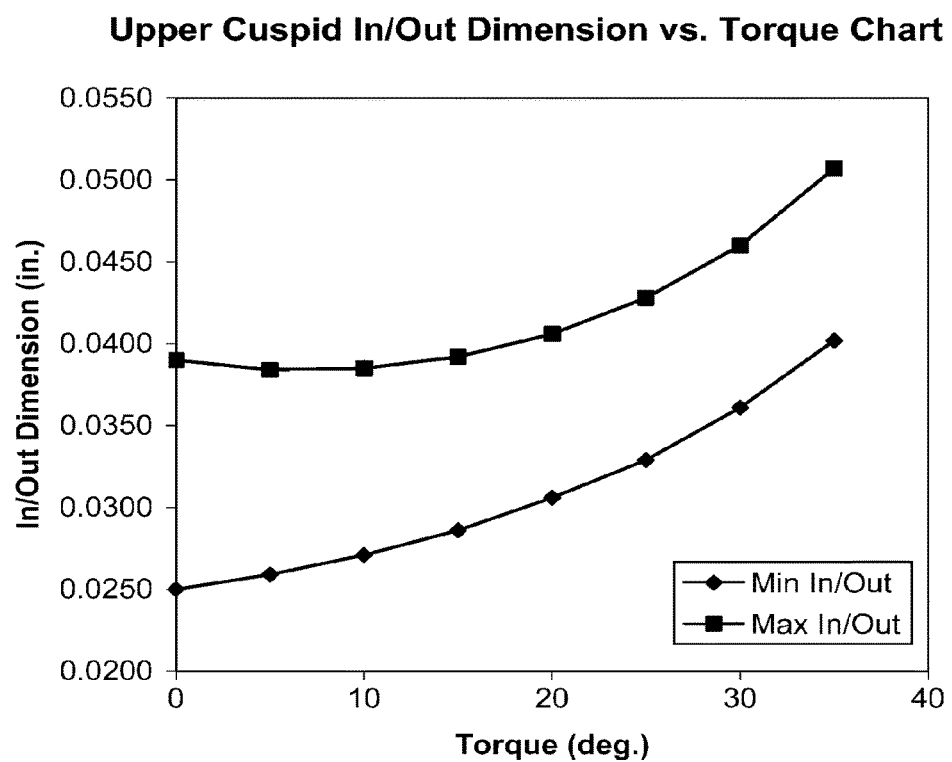
Figure 50:
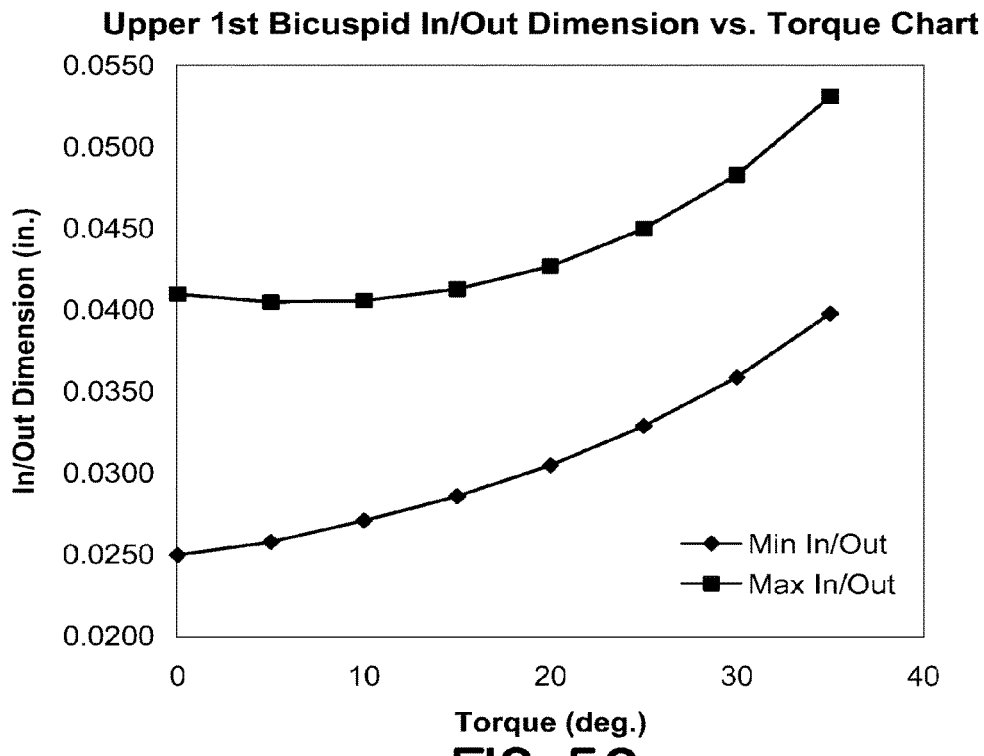
Figure 51:
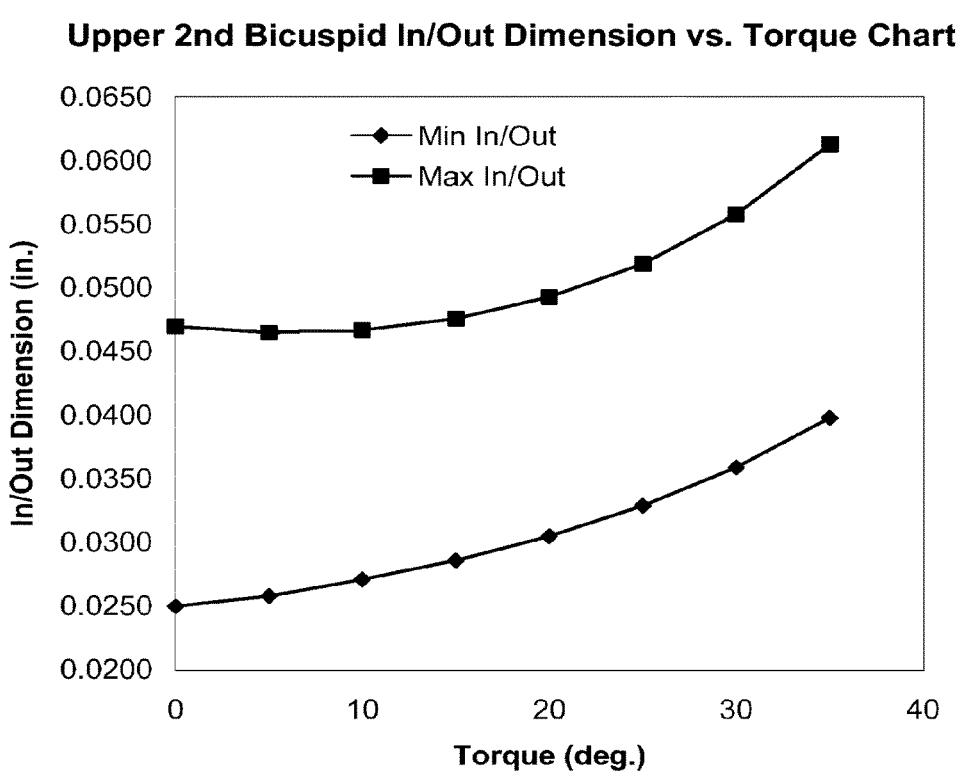
Figure 52:
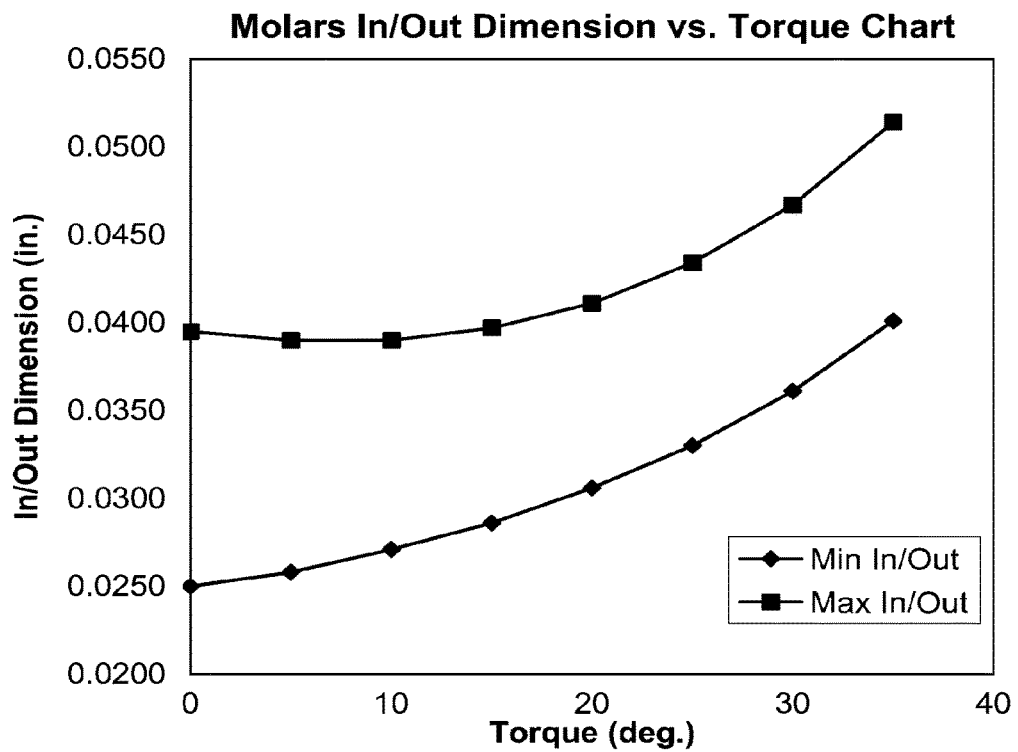
Figure 53:
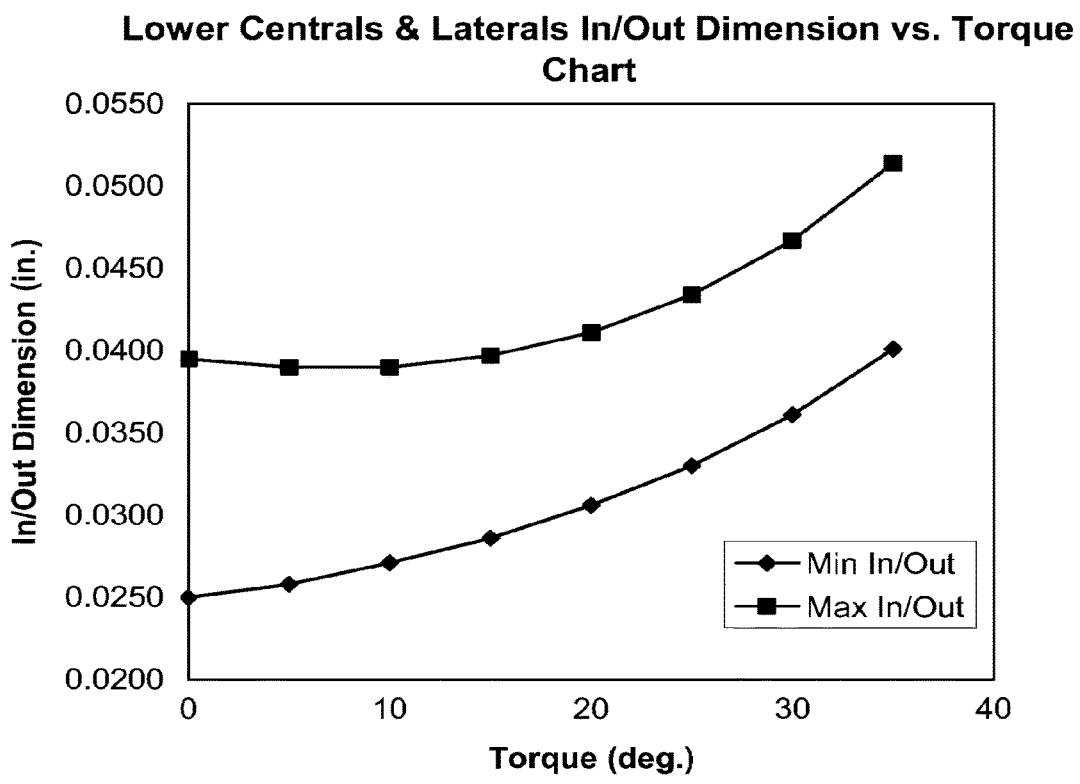
Figure 54:
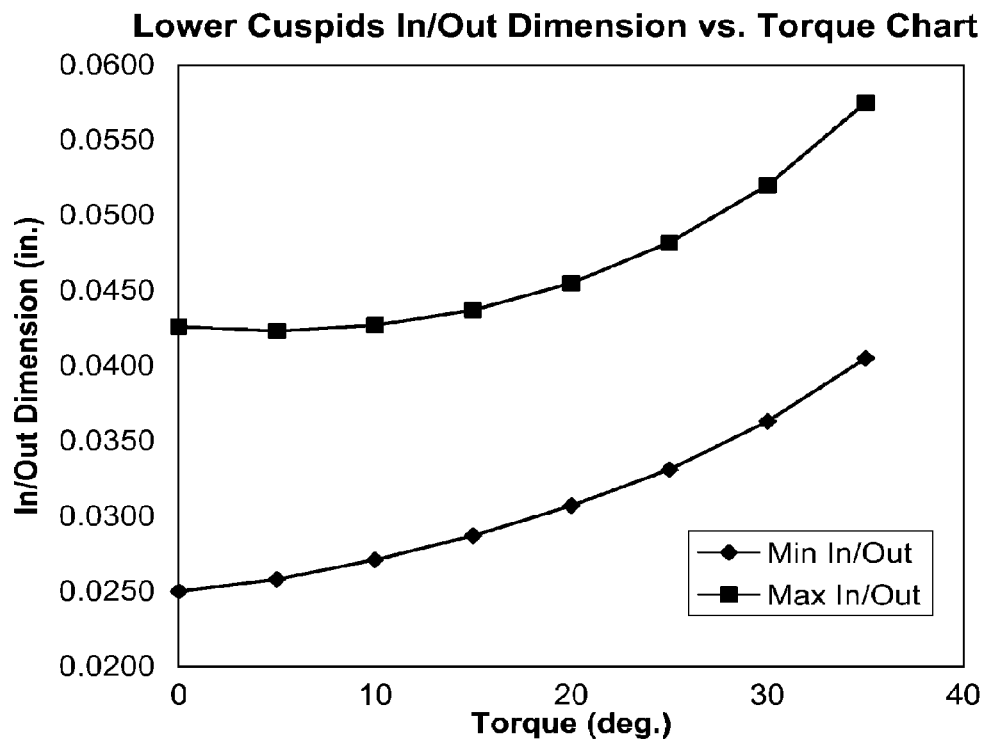
Figure 55:
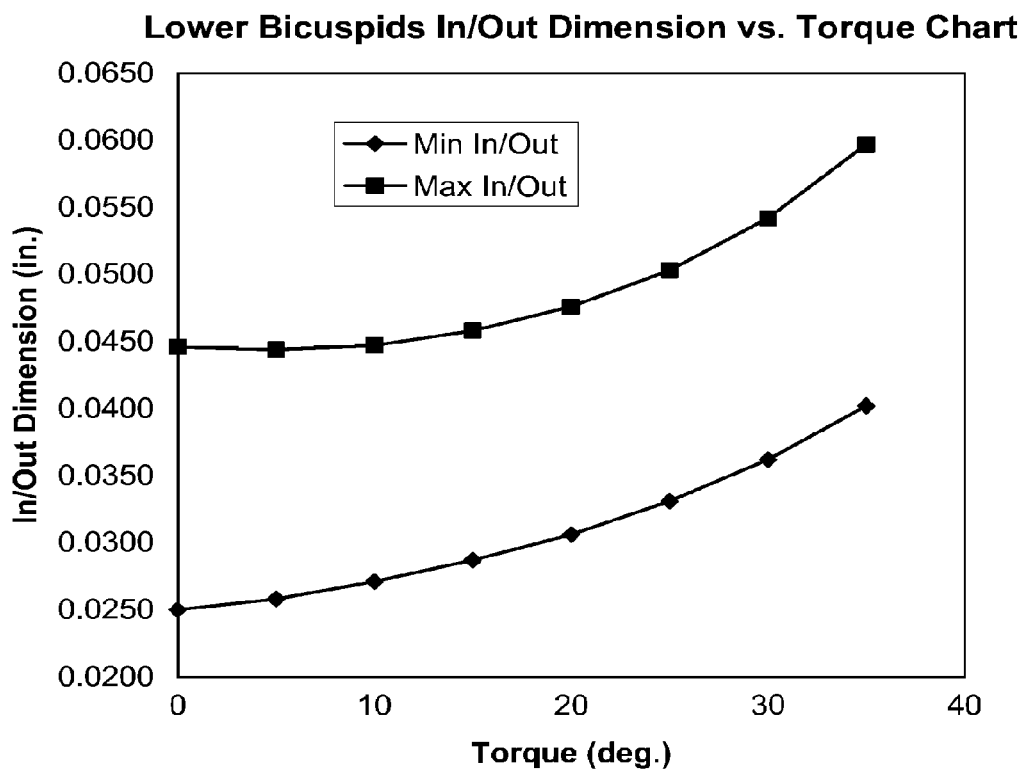

As illustrated in FIG. 44-46, buccal tubes are created for molars using a modification of the process described for bracket slots. Tie-wings are first cut off of the brackets in the molar positions on the bracket card (or mesh panel). The tube typically has an angle cut on it with the same saw used for both the slot cutting for the brackets and the removal of the tie-wings. The angle may be a compound angle, and the slot is parallel this angle. The same logic applies as for the brackets mentioned previously. The slot should not be so deep as to cut into the pad or so shallow as to project beyond the "outer angle". A "lid" will be brazed onto this object at the end of the manufacturing process to complete the buccal tube. Acceptable combinations of slot depth and torque are the same as for the upper 1.sup.st bicuspids (FIG. 50).

Those skilled in the art will appreciate that the present invention described above is exemplary and that aspects thereof may be varied, and that additions and modifications can be made without departing from the principles of the invention. In addition, there are inventive concepts set forth in the disclosure above that may be more appropriately claimed, and/or that applicant reserves the right to claim, in divisional, continuing or otherwise separate applications.

Therefore, the following is claimed:

1. A method of representing a three dimensional tooth object for use in determining an orthodontic setup of the teeth using a computer system, comprising:
   displaying data of a three-dimensional object for at least one molar;
   selecting groove and cusp reference points from the displayed object; and
   defining from the selected groove and cusp reference points lines representative of the orientation of the tooth object, wherein:
   the groove and cusp reference points include a distal-lingual groove point (DLG.Pt), a distal-lingual cusp point (DLC.Pt), a mesial-lingual cusp point (MLC.Pt), a facial cusp point (FC.Pt), and a mesial-facial cusp point (MFC.Pt) from the displayed object; and
   the lines defined from groove and cusp reference points include, from points DLC.Pt and MLC.Pt a labial cusp line segment (LC.Li), from points FC.Pt and MFC.Pt a facial cusp line segment (FC.Li), and from points DLG.Pt and MFC.Pt a line segment Stolar.Li.

2. The method of claim 1 further comprising defining line segments for at least two upper molars, and calculating the occlusion of upper molars based on the defined line segments.

3. The method of claim 1 further comprising:
   defining an occlusal table line segment (OT.Li) perpendicular to LC.Li, coincident with a buccal groove of a tooth, and connecting FC.Li to LC.Li, representing a mid-developmental lobe plane (MDL.Pl).

4. The method of claim 3 further comprising:
   defining the initial mesial-distal positioning of an appliance on the tooth in relation to the mid-developmental lobe plane (MDL.Pl).

5. The method of claim 1 further comprising:
   defining a mandibular computer model of an arrangement of a patient's mandibular teeth on a computer; and
   defining a plane of occlusion from the mandibular computer model by identifying three points on different ones of the teeth on the model.

6. The method of claim 5 wherein:
   the three points include the mesial buccal cusps of the first mandibular molars and the incisal tip of one of the mandibular centrals.

7. The method of claim 1 further comprising:
   producing data representing each of a plurality of a patient's teeth; and
   defining for each tooth a mid-developmental lobe plane.

8. The method of claim 7 wherein the defining includes:
   defining for the tooth, a mid-developmental lobe axis (MDL.Ax) by selection of its extents incisally (IM-DL.Pt) and gingivally (GMDL.Pt);
   defining through MDL.Ax and perpendicular to a mesial-distal axis of the tooth, a mid developmental lobe plane.

9. The method of claim 7 further comprising:
   defining a crown long axis for the tooth in the mid developmental lobe plane.

10. The method of claim 7 further comprising:
    defining a mandibular computer model of an arrangement of a patient's mandibular teeth on a computer; and
    defining a plane of occlusion from the mandibular computer model by identifying three points on different ones of the teeth on the model.

11. The method of claim 10 wherein:
    the three points include the mesial buccal cusps of the first mandibular molars and the incisal tip of one of the mandibular centrals.

12. A method of representing a three dimensional tooth object for use in determining an orthodontic setup of the teeth using a computer system, comprising:
    displaying data of a three-dimensional object for at least one molar;
    selecting groove and cusp reference points from the displayed object; and
    defining from the selected groove and cusp reference points lines representative of the orientation of the tooth object, wherein:
    the selecting includes:
    selecting a mesial-lingual cusp point (MLC.Pt), a distal-lingual cusp point (DLC.Pt), a mesial facial cusp point (MFC.Pt), and a distal-facial cusp point (DFC.Pt), and
    selecting mesial and distal marginal ridges as points MMR.Pt and DMR.Pt, respectively; and
    the defining includes:
    defining from points MLC.Pt and DLC.Pt a labial cusp line segment (LC.Li), from points MFC.Pt and DFC.Pt a facial cusp line segment (FC.Li),
    defining a marginal ridge line segment (MR.Li) as that through points MMR.Pt and DMR.Pt, and
    defining from points MMR.Pt and DLC.Pt a line segment Stolar.Li.

13. The method of claim 12 further comprising:
    calculating the occlusion with lower molars using the line Stolar Li.

14. The method of claim 12 further comprising:
    selecting points MFC.Pt and MLC.Pt to define mesial cusp line segment (MC.Li);
    defining occlusal table line segment (OT.Li) to be parallel to line MC.Li, coincident with the buccal groove, and connecting FC.Li to LC.Li; and
    defining with line OT.Li the mid-developmental lobe plane (MDL.Pl).

15. The method of claim 14 further comprising defining the initial mesial-distal positioning of an appliance on the tooth in relation to the mid-developmental lobe plane (MDL.Pl).

16. A method of representing a three dimensional tooth object for use in determining an orthodontic setup of the teeth using a computer system, comprising:
    displaying data of a three-dimensional object for at least one molar;
    selecting groove and cusp reference points from the displayed object;
    defining from the selected groove and cusp reference points lines representative of the orientation of the tooth object;
    determining an arch shaped arrangement for an orthodontic setup of the teeth, by the steps of:
    generating on a computer a mandibular model of the patient's teeth that includes gingival or jaw shape data;

generating a section through the model through the gingiva or jaw;

selecting points defining facial and lingual boundaries and defining thereby a mandibular trough of the patient, displaying the mandibular trough on a computer display; and calculating a smooth symmetrical bezier curve through the trough between corresponding labial and lingual points;

the curve having handles at the midline and at the distal ends thereof to allow an operator to modify the shape of the bezier curve.

17. The method of claim 16 further comprising:

defining a mandibular computer model of an arrangement of a patient's mandibular teeth on a computer; and defining a plane of occlusion from the mandibular computer model by identifying three points on different ones of the teeth on the model.

18. The method of claim 17 wherein:

the three points include the mesial buccal cusps of the first mandibular molars and the incisal tip of one of the mandibular centrals.

* * * * *